United States Patent [19]

Mori

[11] Patent Number: 5,703,369
[45] Date of Patent: Dec. 30, 1997

[54] POSITRON EMISSION COMPUTED TOMOGRAPHY APPARATUS AND IMAGE RECONSTRUCTION METHOD

[75] Inventor: Shinsuke Mori, Hamamatsu, Japan

[73] Assignee: Hamamatsu Photonics K.K., Hamamatsu, Japan

[21] Appl. No.: 733,575

[22] Filed: Oct. 18, 1996

[30] Foreign Application Priority Data

Oct. 20, 1995 [JP] Japan .................. 7-297816

[51] Int. Cl.[6] .............................. G01T 1/164
[52] U.S. Cl. .................. 250/363.03; 250/363.09; 250/252.1 R
[58] Field of Search .................. 250/363.03, 363.09, 250/252.1 R, 369, 364.04, 363.07

[56] References Cited

U.S. PATENT DOCUMENTS 5,272,343 12/1993 Stearns .......................... 250/363.03

OTHER PUBLICATIONS

Chesler et al, "Calibration of Detector Sensitivity in Positron Cameras," IEEE Transactions on Nuclear Science, vol. 37, No. 2, Apr. 1990, pp. 768–772.

Defrise et al, "A Normalization Technique for 3D PET Data", IOP Publishing Ltd. 1991, pp. 939–952.
Hoffman et al, "Pet System Calibrations and Corrections for Quantitative and Spatially Accurate Images", IEEE Transactions on Nuclear Science, vol. 36, No. 1, Feb. 1989, pp. 1108–1112.

*Primary Examiner*—Don Wong
*Attorney, Agent, or Firm*—Cushman Darby & Cushman IP Group of Pillsbury Madison & Sutro LLP

[57] ABSTRACT

In a positron emission computed tomography apparatus of the present invention, a calibration radiation source is rotated in a measurement space in a detector ring comprised of a lot of photon detectors to perform blank measurement, and sensitivity data are produced on the basis of photon pair detection frequencies obtained for every photon detector pair of the detector ring. Subsequently, an object is set in the measurement space to perform emission measurement, and detection pair identification signals (I, J) from a coincidence counting circuit are subjected to compensation for body motion of the object measured by a position-direction measuring section and then are converted into polar coordinate values of a detector line. At the same time, cumulative data inversely proportional to corresponding values of sensitivity data are produced on the basis of the detection pair identification signals (I, J). Then this cumulative data is cumulated at an address in an address space corresponding to the coordinate values of the detector line to be accumulated as projection data. Therefore, even with an object moving during measurement, an accurate reconstructed image can be attained by effecting body motion correction of the object and accurate sensitivity correction.

14 Claims, 15 Drawing Sheets

5,703,369

POSITRON EMISSION COMPUTED TOMOGRAPHY APPARATUS AND IMAGE RECONSTRUCTION METHOD

BACKGROUND OF THE INVENTION

1. Field of the Invention

The present invention relates to a positron emission CT (Computed Tomography) apparatus and image reconstruction method thereof for detecting photon pairs emitted with annihilation of electron-positron pairs generated by RI (Radio Isotope) radiation sources put in an object to be measured and thereby measuring a substance distribution in the object.

2. Related Background Art

The positron emission computed tomography apparatus (hereinafter referred to as PET) is applied to studies, clinical examinations, etc. of organism or patient, which is an apparatus for imaging a distribution of positron emission nuclides (hereinafter referred to as RI radiation sources) put in a living body to observe a biological function.

The RI radiation sources are used as partly added to an in vivo substance such as a dopamine taking part in neurotransmission or FDG ($^{18}$F-fluorodeoxy glucose) related to metabolism of glucose, or to a drug, for example, being on the way of new development. The PET can observe states of distribution, consumption, or temporal change of such substance in vivo. Furthermore, the PET can also measure basal metabolism of organism including a cerebral blood flow and oxygen consumption.

A detecting section of such PET is comprised of a lot of photon detectors arranged in ring shape (hereinafter referred to as a detector ring), and the object, which is, for example, a human body injected with or inhaling the RI radiation sources, is placed in the detector ring. A positron emitted from an RI radiation source in the object immediately couples with a neighboring electron, resulting in emitting a pair of photons (gamma rays) each having the energy of 511 keV in the opposite directions to each other. Performing coincidence counting of this pair of photons by the detector ring, the apparatus can specify a straight line (hereinafter referred to as a detector line) on which annihilation of the electron-positron pair occurred. The PET accumulates such coincidence counting information and performs an image reconstruction process to produce an image of distribution of RI radiation sources.

The period of time necessary for such measurement by the PET depends upon the half-life of the RI radiation sources, and is occasionally several ten minutes to several hours. Conventionally, the object needed to be fixed both in position and direction during the measurement period. In such cases of taking a long time for measurement, a stationary posture is very painful to a human body or other animal being the object, and the object sometimes moves in the measurement period to change its position and direction.

However, even a small motion of the object during measurement affects accurate measurement. Namely, artifacts due to the motion of the object appear in an image obtained by image reconstruction, thus failing to obtain an accurately reconstructed image.

Even though the object can be kept stationary, the physiological condition of the object is often measured not in an anesthetic condition but in awareness, and the physiological condition thus changes because of stress resulting from the fixed condition for the long time. This change adversely affects the measurement and also damages accurate measurement.

There is thus known technology in which the measurement is carried out as maintaining the physiological condition without fixing the object, that is, with allowing a motion in the position and direction of the object (hereinafter referred to as a body motion), then the body motion is measured during the measurement, and the coincidence counting information is corrected using the body motion information. The prior art concerning such body motion correction is described in detail, for example, in Japanese Laid-open Patent Application No. 2-209133 and Japanese Laid-open Patent Application No. 4-128679.

Rotation or wobbling of the detector ring is utilized in order to raise the spatial measurement resolution of the photon detectors in the detector ring. Conversely, the measurement resolution can also be improved by the motion of the object. Since the body motion correction technology is also effective in this sense, it is possible to obtain a more accurate reconstructed image than before even in the case of the object moving relative to the detector ring.

SUMMARY OF THE INVENTION

In general, there are sensitivity inconsistencies among the many photon detectors constituting the detector ring. Thus, an accurate image of RI radiation source distribution cannot be attained when the image is reconstructed based on raw coincidence counting information (emission data) obtained by detecting photon pairs occurring from the object and accumulating the data. Then sensitivity correction is performed by obtaining sensitivity correction data (blank data) using a radiation source for calibration and dividing the emission data by the blank data.

However, such simple sensitivity correction would be difficult in the case of a moving object. Namely, even though a pair of photons occur at a same position and fly in directions fixed for the object and if the object changes its position and direction, the pair of photons will be received by a different pair of photon detectors having different detection sensitivities from those before change. In spite thereof, the emission data is divided by the same blank data heretofore. Therefore, in addition to the body motion correction technology, the sensitivity correction technology suitable for this case is demanded in order to accurately measure the object in motion.

An object of the present invention is to provide a positron emission CT apparatus and image reconstruction method thereof that can obtain an accurate reconstructed image by body motion correction and accurate sensitivity correction even in the case of the object moving during measurement.

In order to achieve the above object, a positron emission computed tomography apparatus of the present invention comprises: (1) a detector ring comprised of a plurality of photon detectors arranged in ring shape around a predetermined center axis to surround a measurement space, each the photon detector detecting a photon incident thereto from the measurement space to output a photon detection signal corresponding to energy of the photon; (2) a rotating mechanism for relatively rotating a calibration radiation source for emitting a positron to generate a photon pair with annihilation of electron-positron pair, relative to the detector ring about the center axis of the detector ring in the measurement space; (3) a position-direction measuring section for measuring position and direction of an object set in the measurement space, relative to the detector ring, and outputting position-direction data corresponding to the position and direction of the object; (4) a coincidence counting circuit for performing energy discrimination to determine if photons detected by the detector ring are a photon pair generated with annihilation of electron-positron pair in the measurement space, based on the photon detection signals received from the detector ring, and outputting a detector pair identification signal corresponding to a photon detector pair of the detector ring each having detected the two photons constituting the photon pair; (5) a sensitivity data producing section for counting events of detection of photon pair for every photon detector pair of the detector ring each having detected the two photons constituting the photon pair, based on the detector pair identification signal received from the coincidence counting circuit, while without setting the object in the measurement space the rotating mechanism rotates the calibration radiation source relative to the detector ring, and producing and storing sensitivity data corresponding to photon pair detection frequencies for all photon detector pairs of the detector ring; (6) a cumulative data producing section for producing cumulative data having values inversely proportional to values of the sensitivity data taken out from the sensitivity data producing section and, with setting the object in the measurement space, outputting the cumulative data corresponding to the photon detector pair of the detector ring each having detected the two photons constituting the photon pair, based on the detector pair identification signal received from the coincidence counting circuit; (7) coordinate converting means for converting, based on the detector pair identification signal received from the coincidence counting circuit, distance and direction of a detector line being a straight line connecting the photon detector pair of the detector ring each having detected the two photons constituting the photon pair into coordinate values expressed by predetermined polar coordinates set in the measurement space, compensating the coordinate values of the detector line in correspondence to the position and direction of the object, based on the position-direction data received from the position-direction measuring section, and outputting coordinate data corresponding to the coordinate values of the detector line; (8) a projection data accumulating section for cumulating the cumulative data received from the cumulative data producing section at an address of a memory space corresponding to the coordinate values of the detector line, based on the coordinate data received from the coordinate converting means, and accumulating the cumulative data distributed in the memory space, as projection data; and (9) an image reconstructing section for calculating a spatial distribution of photon pair occurrence frequencies with annihilation of electron-positron pair in the object, based on the projection data taken out of the projection data accumulating section, and producing reconstructed image data corresponding to the spatial distribution of photon pair occurrence frequencies.

With such a positron emission computed tomography apparatus, first, the detector ring detects photon pairs occurring from the calibration radiation source rotated by the rotating mechanism and the sensitivity data producing section acquires the sensitivity data based on the photon pair detection frequencies obtained for all photon detector pairs as to the plurality of photon detectors constituting the detector ring.

Subsequently, upon measurement of the object, the coincidence counting circuit outputs the detector pair identification signal indicating the photon detector pair having detected a photon pair to the coordinate converting section, the signal is compensated for displacements of position and direction of the object measured by the position-direction measuring section, the coordinate converting means outputs coordinate values expressing the detector line connecting the photon detector pair by polar coordinates, and the cumulative data producing section outputs the cumulative data inversely proportional to the sensitivity data corresponding to the detector pair identification signal.

Then the projection data accumulating section cumulates the cumulative data output from the cumulative data producing section in the projection data stored at the address in the address space corresponding to the coordinate values output from the coordinate converting section. Here, the projection data accumulated in the projection data accumulating section is data having already been subjected to the both body motion correction and sensitivity correction, and thus, the image reconstructing section reconstructs an image, based on this projection data.

Here, the positron emission computed tomography apparatus of the present invention preferably further comprises an image displaying section for displaying a reconstructed image indicating the spatial distribution of photon pair occurrence frequencies with annihilation of electron-positron pair in the object, based on the reconstructed image data taken out of the image reconstructing section.

In the positron emission computed tomography apparatus of the present invention, the cumulative data section preferably produces and stores the cumulative data having the values inversely proportional to the values of the sensitivity data corresponding to all photon detector pairs of the detector ring before the detector ring detects the photon pair for the object set in the measurement space.

In the positron emission computed tomography apparatus of the present invention, the cumulative data section preferably produces and outputs the cumulative data having the values inversely proportional to the values of the sensitivity data corresponding to the photon detector pair of the detector ring each having detected the two photons constituting the photon pair every time the detector ring detects the photon pair for the object set in the measurement space.

Further, in the positron emission computed tomography apparatus of the present invention, without intentionally setting the calibration radiation source in the measurement space and with setting the object containing a positron emission nuclide therein, the cumulative data section preferably outputs, as emission data, the cumulative data corresponding to the photon detector pair of the detector ring each having detected the two photons constituting the photon pair, based on the detector pair identification signal received from the coincidence counting circuit.

In this case, with setting the object intentionally containing no positron emission nuclide in the measurement space and with rotating the calibration radiation source relative to the detector ring by the rotating mechanism, the cumulative data section desirably outputs, as transmission data, the cumulative data corresponding to the photon detector pair of the detector ring each having detected the two photons constituting the photon pair, based on the detector pair identification signal received from the coincidence counting circuit.

More desirably, the projection data accumulating section cumulates the emission data and the transmission data received from the cumulative data producing section independently of each other at two types of addresses in the memory space corresponding to the coordinate values of the detector line, based on the coordinate data received from the coordinate converting means, and the image reconstructing section calculates a ratio of the emission data and the transmission data as the spatial distribution of photon pair occurrence frequencies, based on the projection data taken out of the projection data accumulating section.

Next, in order to achieve the above object, the image reconstructing method of positron emission computed tomography of the present invention is an image reconstructing method of positron emission computed tomography for detecting photon pairs occurring with annihilation of electron-positron pair in a measurement space and measuring a spatial distribution of occurrence frequencies of the photon pairs by a detector ring comprised of a plurality of photon detectors arranged in ring shape around a predetermined center axis to surround the measurement space, each the photon detector detecting a photon incident thereto from the measurement space to output a photon detection signal corresponding to energy of the photon, and a coincidence counting circuit for performing energy discrimination to determine if photons detected by the detector ring are a photon pair occurring with annihilation of electron-positron pair in the measurement space, based on the photon detection signals output from the detection ring, and outputting a detector pair identification signal corresponding to a photon detector pair of the detector ring each having detected two photons constituting the photon pair, comprising: (1) a first step of, without setting an object in the measurement space, relatively rotating a calibration radiation source for emitting a positron to generate a photon pair with annihilation of electron-positron pair, relative to the detector ring about the center axis of the detector ring in the measurement space, thereafter counting events of detection of photon pair for every photon detector pair of the detector ring each having detected the two photons constituting the photon pair, based on the detector pair identification signal output from the coincidence counting circuit, and producing and storing sensitivity data corresponding to photon pair detection frequencies for all photon detector pairs of the detector ring; (2) a second step of, with setting the object in the measurement space, measuring position and direction of the object set in the measurement space, relative to the detector ring, converting, based on the detector pair identification signal output from the coincidence counting circuit, distance and direction of a detector line being a straight line connecting the photon detector pair of the detector ring each having detected the two photons constituting the photon pair into coordinate values expressed by predetermined polar coordinates set in the measurement space, producing cumulative data having values inversely proportional to values of the sensitivity data produced in the first step, cumulating the cumulative data at an address of a memory space corresponding to the coordinate values of the detector line compensated in correspondence to the position and direction of the object, and accumulating the cumulative data distributed in the memory space, as projection data; and (3) a third step of calculating a spatial distribution of photon pair occurrence frequencies with annihilation of electron-positron pair in the object, based on the projection data produced in the second step, and producing reconstructed image data corresponding to the spatial distribution of photon pair occurrence frequencies.

In the image reconstructing method of positron emission computed tomography as described above, every time a photon detector pair detects a photon pair occurring from the object, the cumulative data inversely proportional to the sensitivity data obtained in the first step is cumulated in the second step at an address in the address space corresponding to the coordinate values expressed by the polar coordinates set in the measurement space as compensated for displacements of the position and direction of the object as to the detection line connecting the photon detector pair. The projection data accumulated herein is data having already been subjected to the both body motion correction and sensitivity correction, and thus, the image reconstructing process based on this projection data is carried out in the third step.

Here, in the image reconstructing method of positron emission computed tomography of the present invention, the third step preferably further comprises displaying a reconstructed image indicating the spatial distribution of photon pair occurrence frequencies with annihilation of electron-positron pair in the object, based on the reconstructed image data.

Additionally, in the image reconstructing method of positron emission computed tomography of the present invention, the second step preferably comprises producing and storing the cumulative data having the values inversely proportional to the values of the sensitivity data corresponding to the all photon detector pairs of the detector ring before the detector ring detects the photon pair for the object set in the measurement space.

Additionally, in the image reconstructing method of positron emission computed tomography of the present invention, the second step preferably comprises producing and outputting the cumulative data having the values inversely proportional to the values of the sensitivity data corresponding to the photon detector pair of the detector ring each having detected the two photons constituting the photon pair every time the detector ring detects the photon pair for the object set in the measurement space.

Further, in the image reconstructing method of positron emission computed tomography of the present invention, the second step preferably comprises outputting, as emission data, the cumulative data corresponding to the photon detector pair of the detector ring each having detected the two photons constituting the photon pair, based on the detector pair identification signal received from the coincidence counting circuit, without intentionally setting the calibration radiation source in the measurement space and with setting the object containing a positron emission nuclide therein.

In this case, the second step desirably comprises outputting, as transmission data, the cumulative data corresponding to the photon detector pair of the detector ring each having detected the two photons constituting the photon pair, based on the detector pair identification signal received from the coincidence counting circuit, with setting the object intentionally containing no positron emission nuclide in the measurement space and with rotating the calibration radiation source relative to the detector ring.

Further, the second step more desirably comprises cumulating the emission data and the transmission data independently of each other at two types of addresses in the memory space corresponding to the coordinate values of the detector line, based on the coordinate data, and calculating a ratio of the emission data and the transmission data as the spatial distribution of photon pair occurrence frequencies, based on the projection data.

The present invention will be more fully understood from the detailed description given hereinbelow and the accompanying drawings, which are given by way of illustration only and are not to be considered as limiting the present invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will be apparent to those skilled in the art from this detailed description.

DESCRIPTION OF THE PREFERRED EMBODIMENTS

Figure 1:
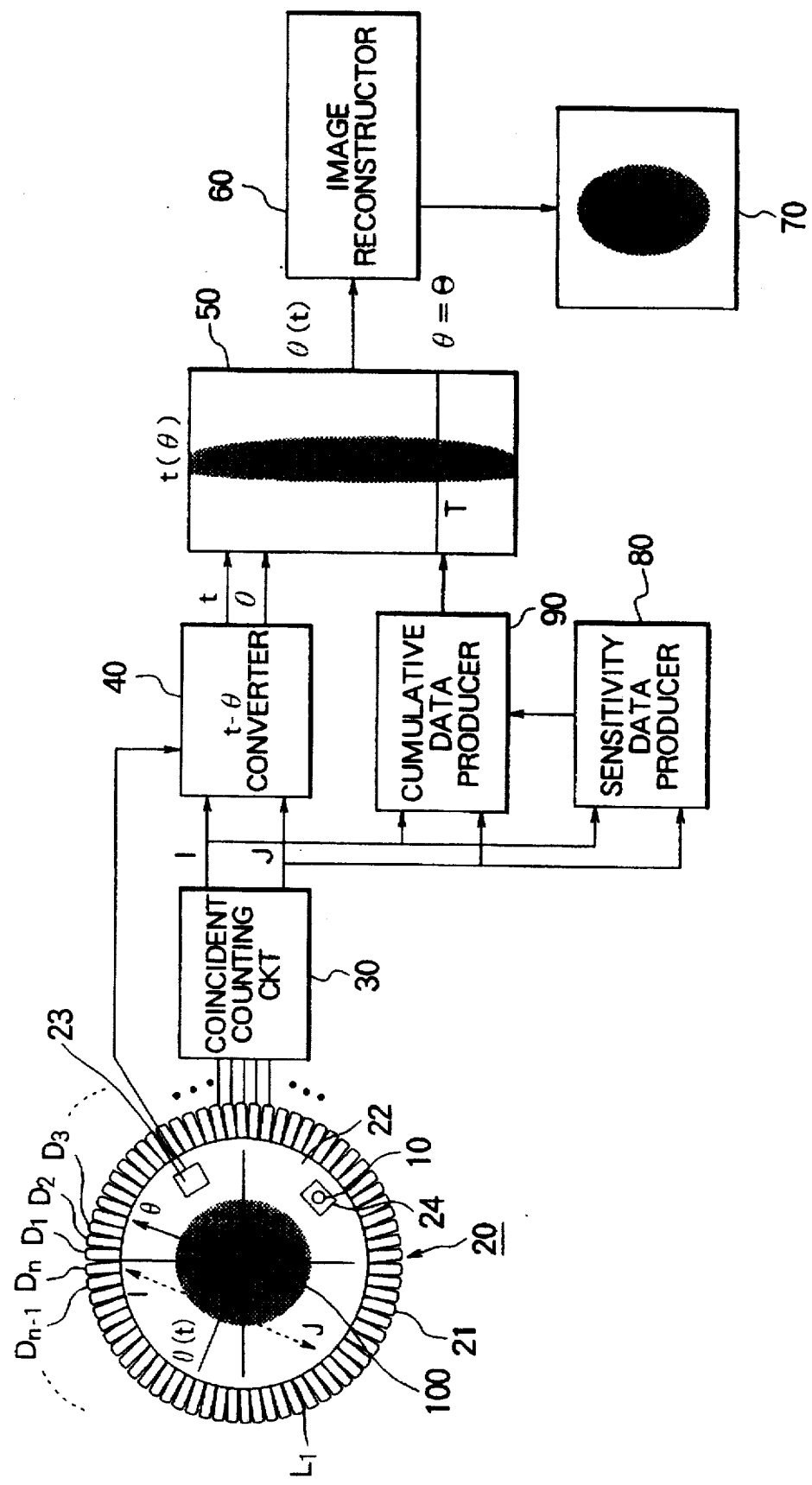
FIG. 1 is a block diagram to show the system structure of a two-dimensional positron emission computed tomography apparatus (2D-PET) of the first embodiment according to the present invention.

The structure and operation of the embodiments of the positron emission computed tomography apparatus and image reconstruction method thereof according to the present invention will be described in detail with reference to FIG. 1 to FIG. 15. It is noted herein that in the description with the drawings same symbols denote same elements and redundant description will be omitted. It is also understood that dimensional ratios in the drawings do not always coincide with those in the description.

First Embodiment

The two-dimensional positron emission computed tomography apparatus (the 2D-PET) of the present embodiment is used as moving the object relative to the detector ring kept stationary. FIG. 1 is a block diagram to show the system structure of the 2D-PET.

As shown in FIG. 1, this 2D-PET comprises (1) a detecting section 20 having a detector ring 21 comprised of a lot of photon detectors, arranged in ring shape, for detecting photons, a body motion measuring section 23 for measuring the position and direction of object 100 to output position-direction data, a rotating mechanism 24 for rotating a radiation source for calibration 10 about the center axis of the detector ring 21 in a measurement space 22, etc. and (2) a coincidence counting circuit 30 for determining whether a photon pair detected by the detector ring 21 is one occurring with annihilation of an electron-positron pair, identifying a photon detector pair having detected the photon pair, and outputting detector pair identification signals.

The 2D-PET further comprises (3) a sensitivity data producing section 80 for producing sensitivity data concerning all of the detector pair identification signals received from the coincidence counting circuit 30, (4) a cumulative data producing section 90 for outputting cumulative data inversely proportional to values of the sensitivity data received from the sensitivity data producing section 80, corresponding to the detector pair identification signals received from the coincidence counting circuit 30, and (5) a t–θ converting section 40 for performing conversion of coordinates to obtain coordinate values (t, θ) as expressing a straight line (detector line) connecting each photon detector pair, identified by the coincidence counting circuit 30, with each other by polar coordinates.

The 2D-PET further comprises (6) a t–θ memory 50 for cumulating the cumulative data received from the cumulative data producing section 90 at an address of its memory space corresponding to the coordinate values (t, θ) after converted into by the t–θ converting section 40 to accumulate it as projection data, (7) an image reconstructing section 60 for producing reconstructed image data based on the projection data accumulated in the t–θ memory 50, and (8) an image displaying section 70 for displaying a reconstructed image based on the reconstructed image data produced by the image reconstructing section 60.

The detector ring 21 is composed of n photon detectors $D_k$ (k=1, 2, 3, . . . , n) arranged in ring shape, and a light-receiving surface of each photon detector is arranged to face the object 100 placed in the measurement space 22 located around the center axis. The photon detectors $D_k$ (k=1, 2, 3, . . . , n) each are connected by a signal line to the coincidence counting circuit 30. When either one photon detector in the detector ring 21 detects a photon, a signal according to energy of the photon is sent through the signal line to the coincidence counting circuit 30.

At this time, the coincidence counting circuit 30 recognizes, based on signals from the respective photon detectors in the detector ring 21, that two photon detectors in the detector ring 21 coincidently detect a photon pair with the predetermined photon energy (511 keV) emitted from a positron emission nuclide (an RI radiation source) contained in the object 100, and then outputs detector identification signals (I, J), as photon detection signals, respectively indicating these two photon detectors at that time.

These detector identification signals (I, J) are supplied to the t–θ converting section 40 to be converted into a mapping position (T, Θ) on the t–θ plane with two variables (t, θ) each being the coordinate axes used for expressing a straight line L1 connecting two photon detectors having detected a photon pair by polar coordinates in the measurement space 22 in the detector ring 21. Here, T represents the distance between this straight line and the coordinate origin, and Θ an angle of the normal line from the coordinate origin to this straight line with respect to the principal axis of the coordinate system.

The t–θ memory 50 cumulates a predetermined value in the projection data stored at an address corresponding to this coordinate position (T, Θ). In this manner, the coincidence counting information about a pair of photons occurring at an RI radiation source 10 is stored in the t−θ memory 50. The coincidence counting information on the many photon pairs thus occurring at the RI radiation sources and detected by the detector ring 21 is accumulated as projection data in the t−θ memory 50.

Figure 2:
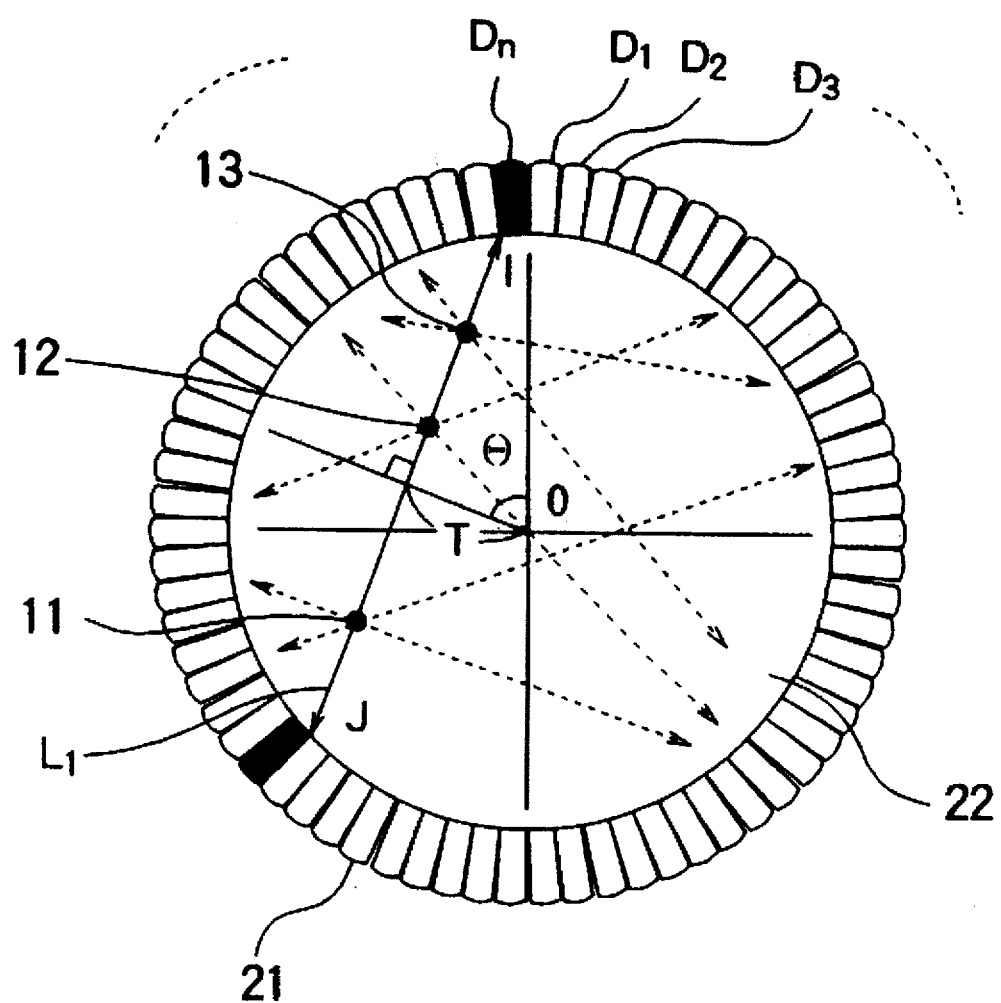
FIG. 2 is a plan view to show the structure of a detector ring in the 2D-PET of FIG. 1.

FIG. 2 is a plan view to explain the photon pair detection in the detector ring of the 2D-PET and the image reconstruction. As shown in FIG. 2, an image to represent a distribution of the RI radiation sources 11 as observed in the term of the direction Θ (the direction of the straight line L1 in FIG. 3) of the polar coordinate system set in the measurement space 22 in the detector ring 21 is reconstructed by the image reconstructing section 60 from the projection data corresponding to each point on θ=Θ and t=T in the polar coordinate system, that is, corresponding to the photon pair emitted along the direction of the straight line L1 among the photon pairs emitted in arbitrary directions from the RI radiation sources 11 to 13 located in the object 100, and this reconstructed image is displayed in the image displaying section 70.

Figure 3:
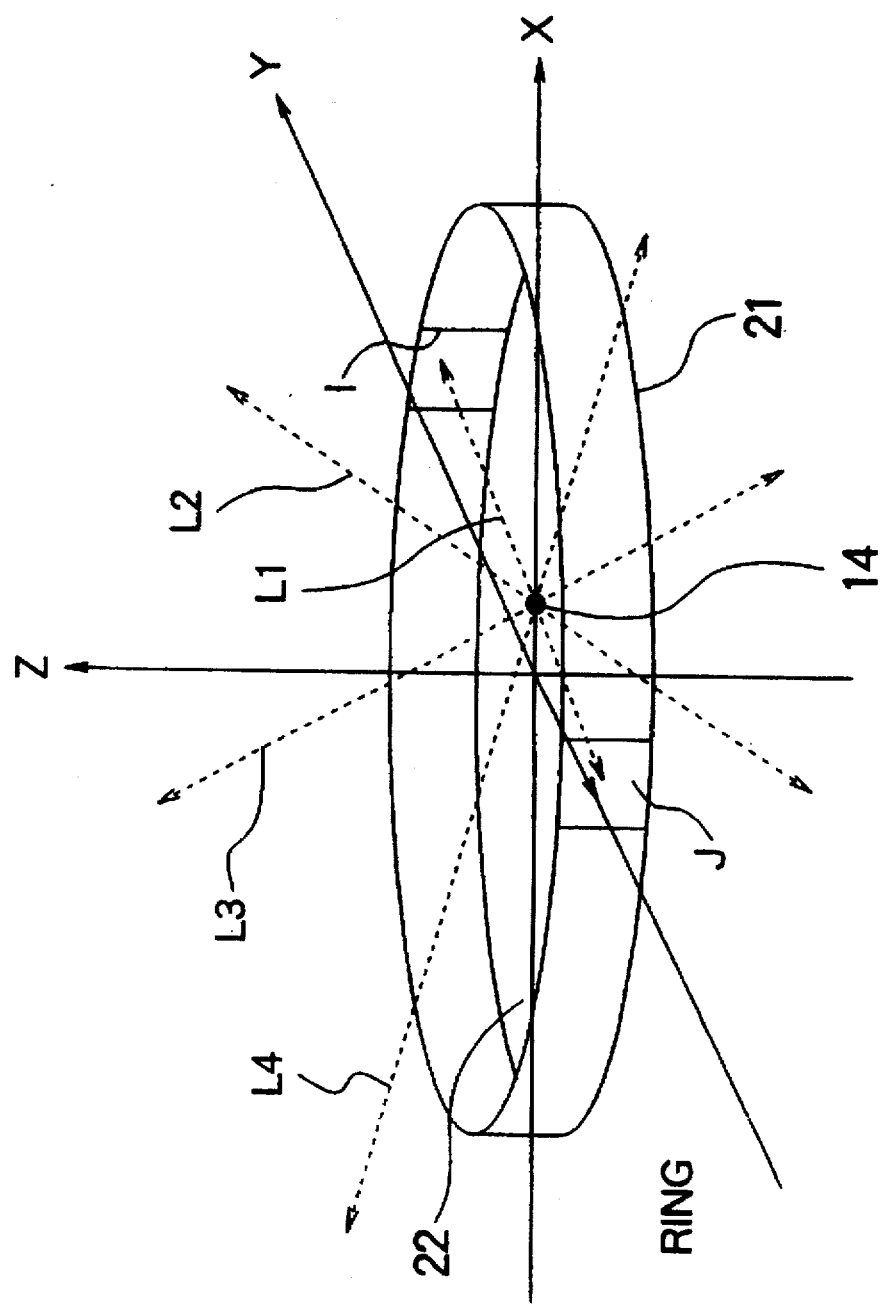
FIG. 3 is a perspective view to explain detection of photon pair in the detector ring of FIG. 2.

It is, however, noted that all photon pairs occurring in the measurement space are not detected. FIG. 3 is a perspective view to explain the detection of photon pair in the detector ring. In FIG. 3, the photodetector ring is schematically shown in cylindrical shape in order to clearly show tracks of photon pairs. The photon pairs emitted from the RI radiation sources 14 contained in the object 100 are emitted from every position where an RI radiation source 14 exists and fly in every direction. Among them, only photon pairs occurring on a reference surface (XY plane) on which the detector ring 21 is located and flying in directions along the reference surface can be detected by the detector ring 21.

For example, as shown in FIG. 3, even though occurring from the RI radiation source 14 existing in the detector ring 21, photon pairs flying in the directions L2 to L4 other than the directions along the reference surface of the detector ring 21 are not detected. A photon pair flying in the directions L1 along the reference surface of the detector ring 21 is detected by two photon detectors I, J (I, J=1, 2, . . . , n) to be converted into (T, Θ) in the t−θ converting section 40, and the predetermined value is added to the projection data at a corresponding address of the t−θ memory 50.

Figure 4:
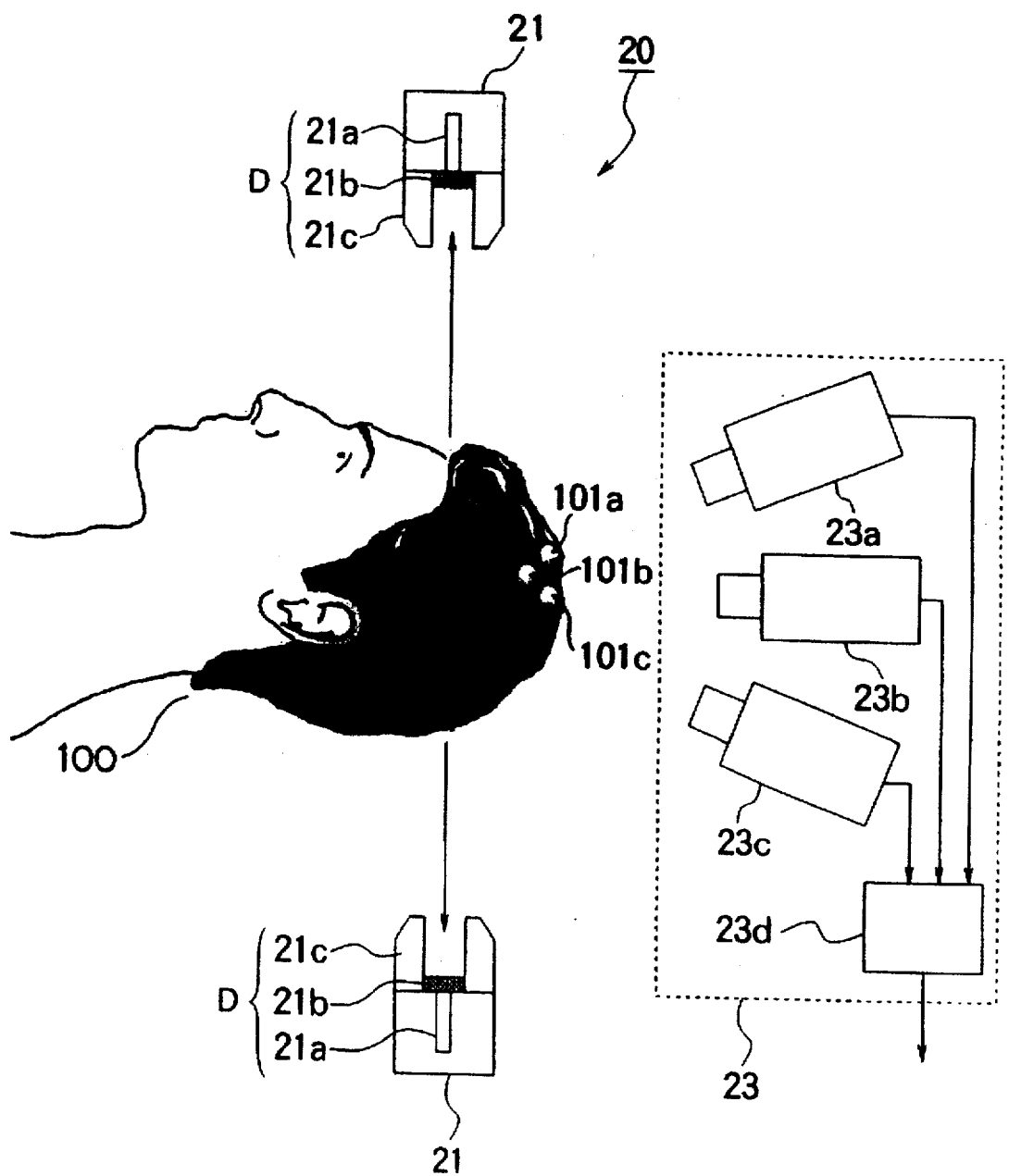
FIG. 4 is a sectional view to show the structure of a detecting section in the 2D-PET of FIG. 1.

FIG. 4 is a sectional view to show the structure of the detecting section in the 2D-PET. As shown in FIG. 4, the detecting section 20 comprises a detector ring 21 constructed as a monolayer ring comprised of many photon detectors D, and a body motion measuring section (position-direction measuring section) 23 for measuring the position and direction of the object 100.

The detector ring 21 detects photon pairs incident thereto from the measurement space 22 defined inside and outputs photon detection signals to the coincidence counting circuit 30. This detector ring 21 is constructed in such structure that a monolayer ring is provided and that a plurality of photon detectors D are arranged in ring shape in the monolayer ring. Each photon detector D is comprised of a PMT (Photo-Multiplier Tube) 21a, a scintillator 21b set on a light-receiving surface of the PMT 21a, and screening shields 21c set on the side surfaces of the scintillator 21b. The light-receiving surface of each photon detector D is faced to the measurement space 22 in which the object 100 is placed. The screening shields 21c are provided for preventing a photon pair from leaking to the outside of the measurement space 22.

The body motion measuring section 23 measures the position and direction of the object 100 set in the measurement space 22 and outputs the position-direction data to the t−θ converting section 40. This body motion measuring section 23 is comprised of, for example, three optical distance-measuring sensors 23a to 23c each consisting of a light emitting device and a light receiving device, and a body motion data processing section 23d for outputting the position-direction data based on outputs therefrom.

The distance-measuring sensors 23a to 23c each are positioned in fixed relative positional relation to the detector ring 21, and they project respective light beams toward three markers 101a to 101c set at selected positions of the object 100 (on the head of a human body being the object 100 in FIG. 4) to receive reflected light therefrom and measure distances to these markers 101a to 101c. The distance data obtained from each of the three distance-measuring sensors 23a to 23c is supplied to the body motion data processing section 23d to obtain the position and direction of the object 100.

Image pickup cameras may be used as the body motion measuring section 23, and the position and direction of the object 100 may be obtained by analyzing images obtained thereby. As another example, acceleration sensors set at selected positions of the object 100 may be used as the body motion measuring section 23, and in this case, the position and direction of the object 100 can be obtained based on outputs from the acceleration sensors.

Figure 5A:
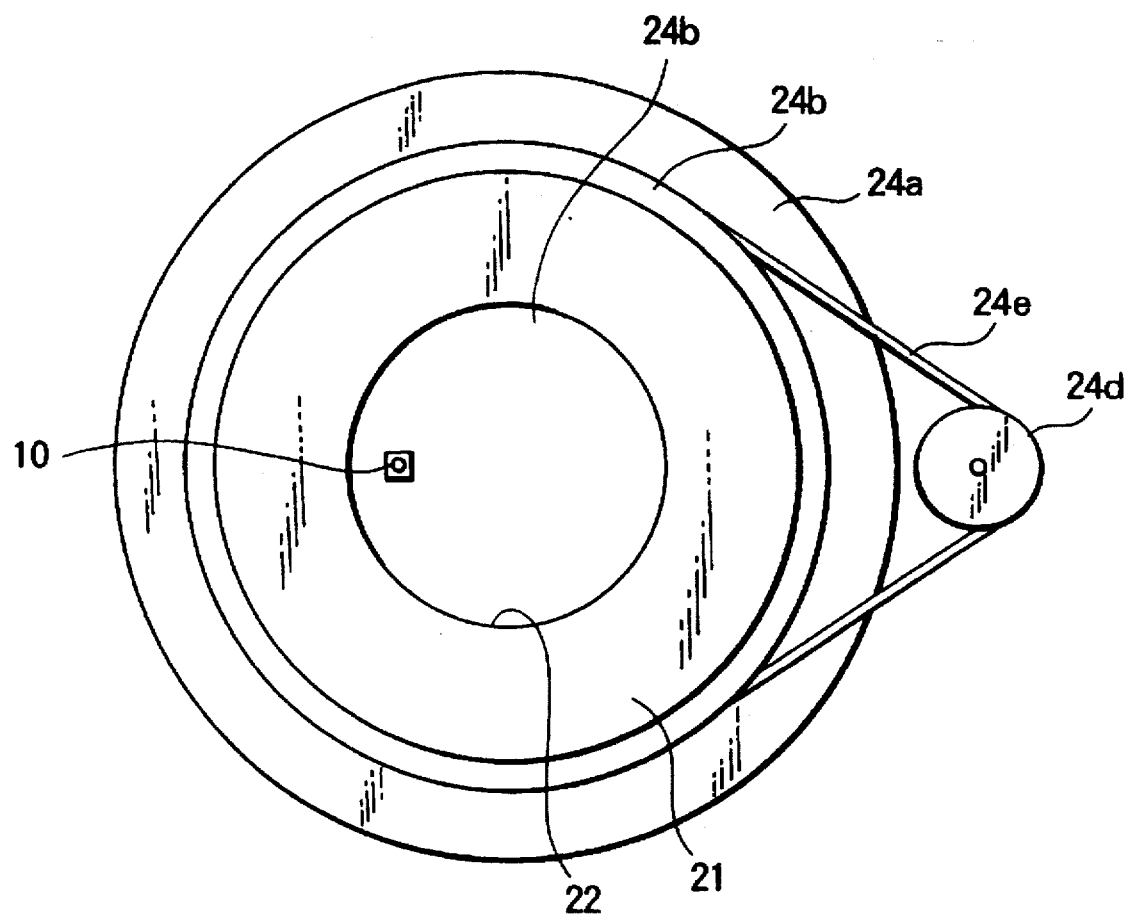
FIG. 5A is a plan view to show the structure of a rotating mechanism, observed from the detector ring side in the 2D-PET.
Figure 5B:
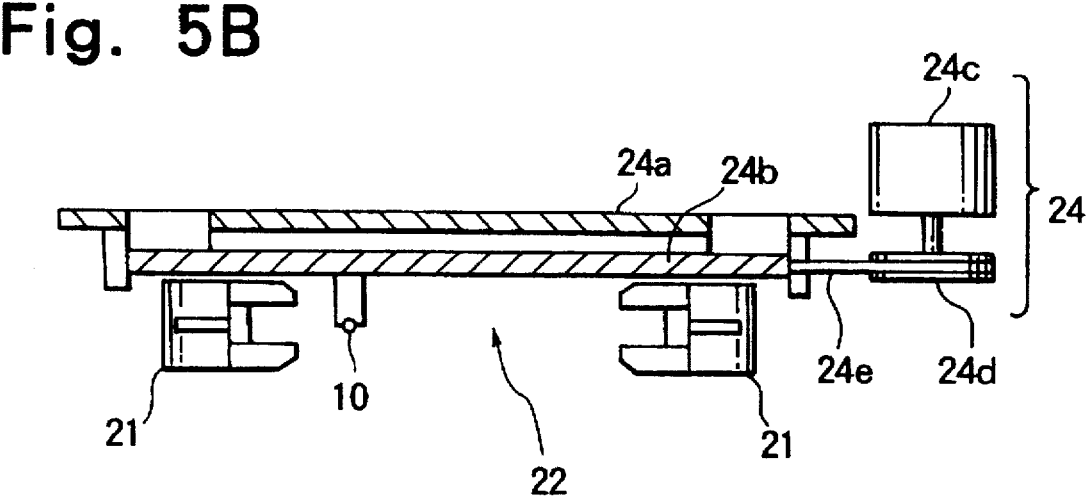
FIG. 5B is a sectional view to show the structure of the rotating mechanism of FIG. 5A.

FIG. 5A is a plan view to show the structure of the rotating mechanism, as observed from the side of the detector ring 21, in the 2D-PET, and FIG. 5B is a sectional view to show the structure of the rotating mechanism. As shown in FIG. 5A and FIG. 5B, the detecting section 20 further comprises a radiation source for calibration 10 used for blank measurement and transmission measurement except for emission measurement as described below, and a rotating mechanism 24 for rotating the calibration radiation source 10 about the center axis of the detector ring 21.

The rotating mechanism 24 is comprised of, for example, a generally disk-shaped gantry base 24a fixed as opposed to the detector ring 21, a ring base (support mechanism) 24b set as rotatable about the center axis of the detector ring 21 on the gantry base 24a and supporting the calibration radiation source 10 in the measurement space 22, a small disk 24d having a smaller diameter than a diameter of the ring base 24b and set as directly connected to a rotary axis of a motor 24c, and a rotary belt 24e connecting guide rails of the ring base 24b and small disk 24d with each other to transmit the rotational force of the motor 24c to the ring base 24b.

The rotary axis of the motor 24c is rotated upon blank measurement and upon transmission measurement, and the rotational force of the motor 24c, transmitted through the small disk 24d and rotary belt 24e, rotates the ring base 24b about the center axis of the detector ring 21. Thus, the calibration radiation source 10, fixed on the measurement space side of the ring base 24b, moves so as to face each light-receiving surface of the plural photon detectors D in the measurement space 22.

The calibration radiation source 10, when used (upon blank measurement and upon transmission measurement), rotates about the center axis of the detector ring 21 on the reference surface of the detector ring 21, whereby a photon detector pair detects each pair of photons flying on the reference surface of the detector ring 21 out of those occurring from the calibration radiation source 10. On the other hand, the radiation source 10, when not used (upon emission measurement), is withdrawn up to a position where no photon pair from the calibration radiation source reaches the photon detectors. Alternatively, the calibration radiation source 10 may be taken away form this apparatus.

Figure 6:
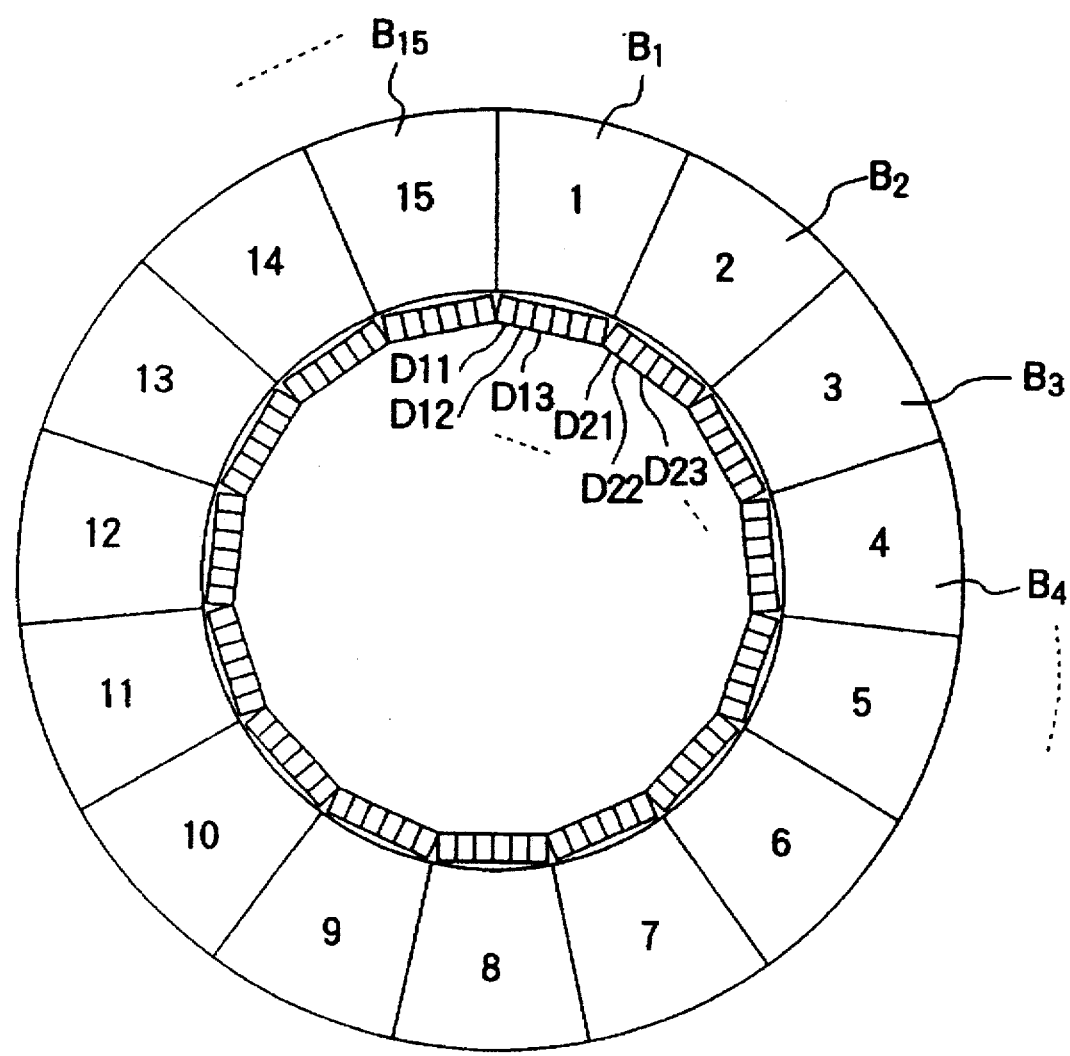
FIG. 6 is a plan view to show the structure of the detector ring in the case where the 2D-PET of FIG. 1 is constructed as a block type PET.

FIG. 6 is a plan view to show the structure of the detector ring in a 2D-PET constructed as a block type PET. Because of ease to fabricate and low cost, the photon detectors in the detector ring may be formed in block form. In the detector ring of this type, as shown in FIG. 6, a plurality of blocks $B_p$ are arranged in ring shape and a number of photon detectors $D_{pq}$ (p=1, 2, 3, ... ; q=1, 2, 3, ... ) are arranged in parallel on the inner surfaces of these plural blocks $B_p$. This block type PET is different simply in the arrangement of the photon detectors, and the operation principle, accumulation of projection data, and image reconstruction are the same as explained above.

Figure 7:
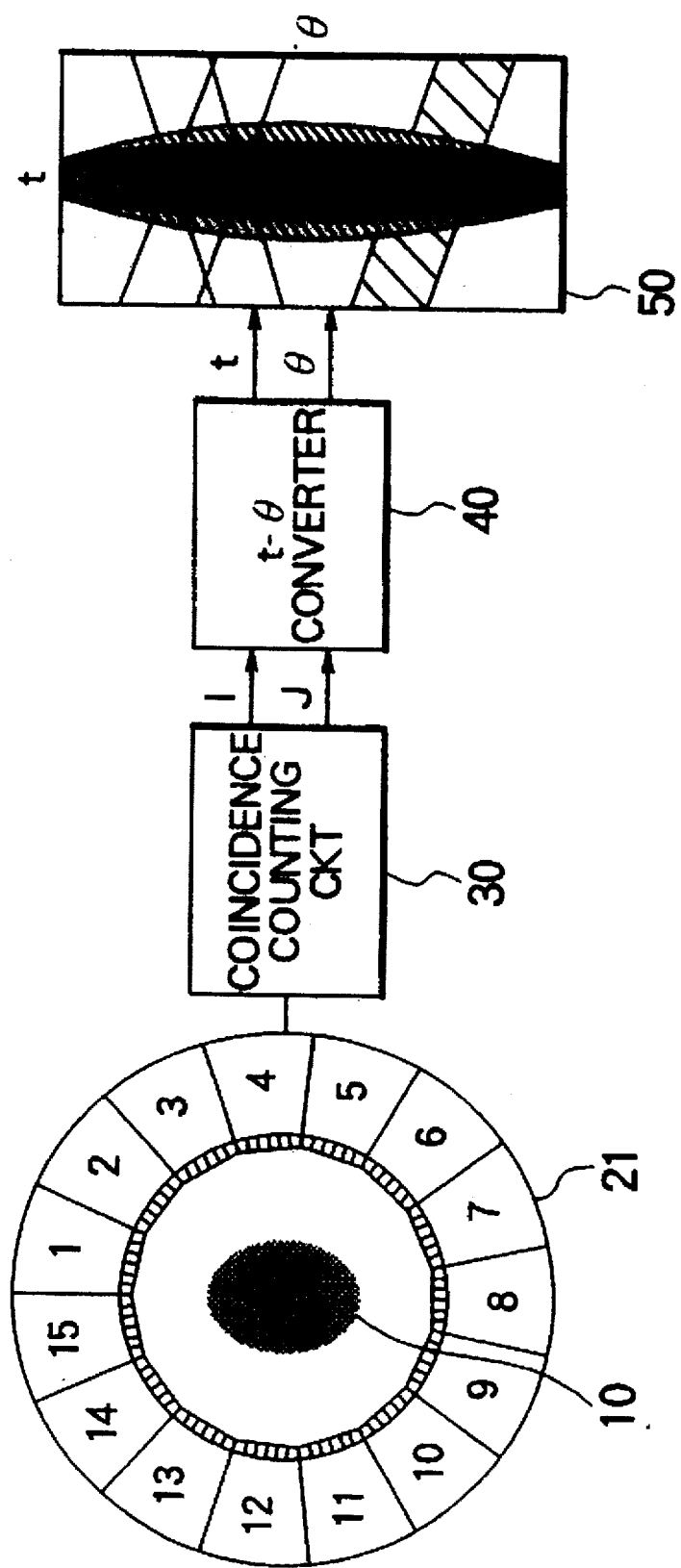
FIG. 7 is a block diagram to explain emission measurement in the 2D-PET of FIG. 6.
Figure 8:
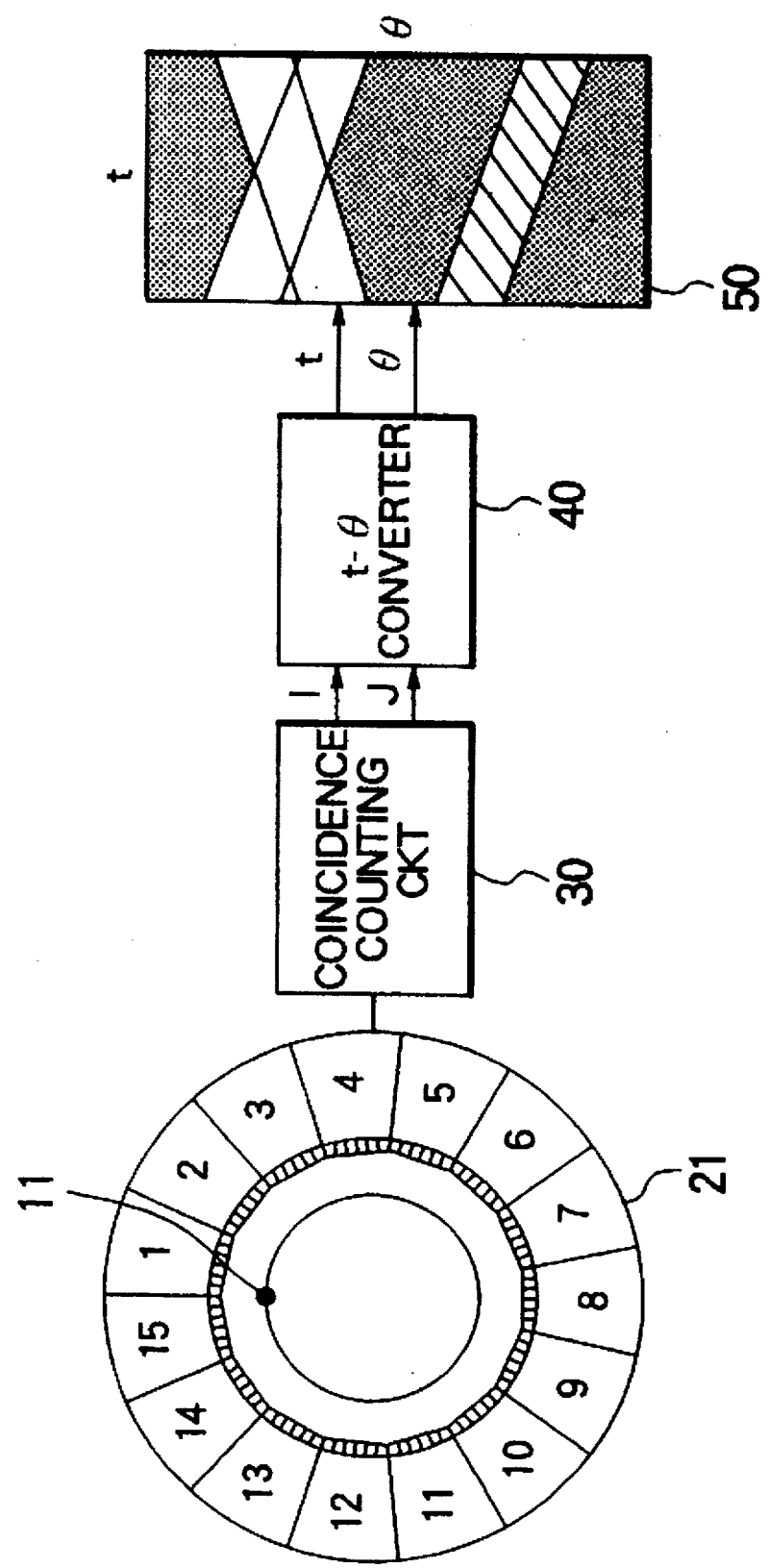
FIG. 8 is a block diagram to explain blank measurement in the 2D-PET of FIG. 6.
Figure 9:
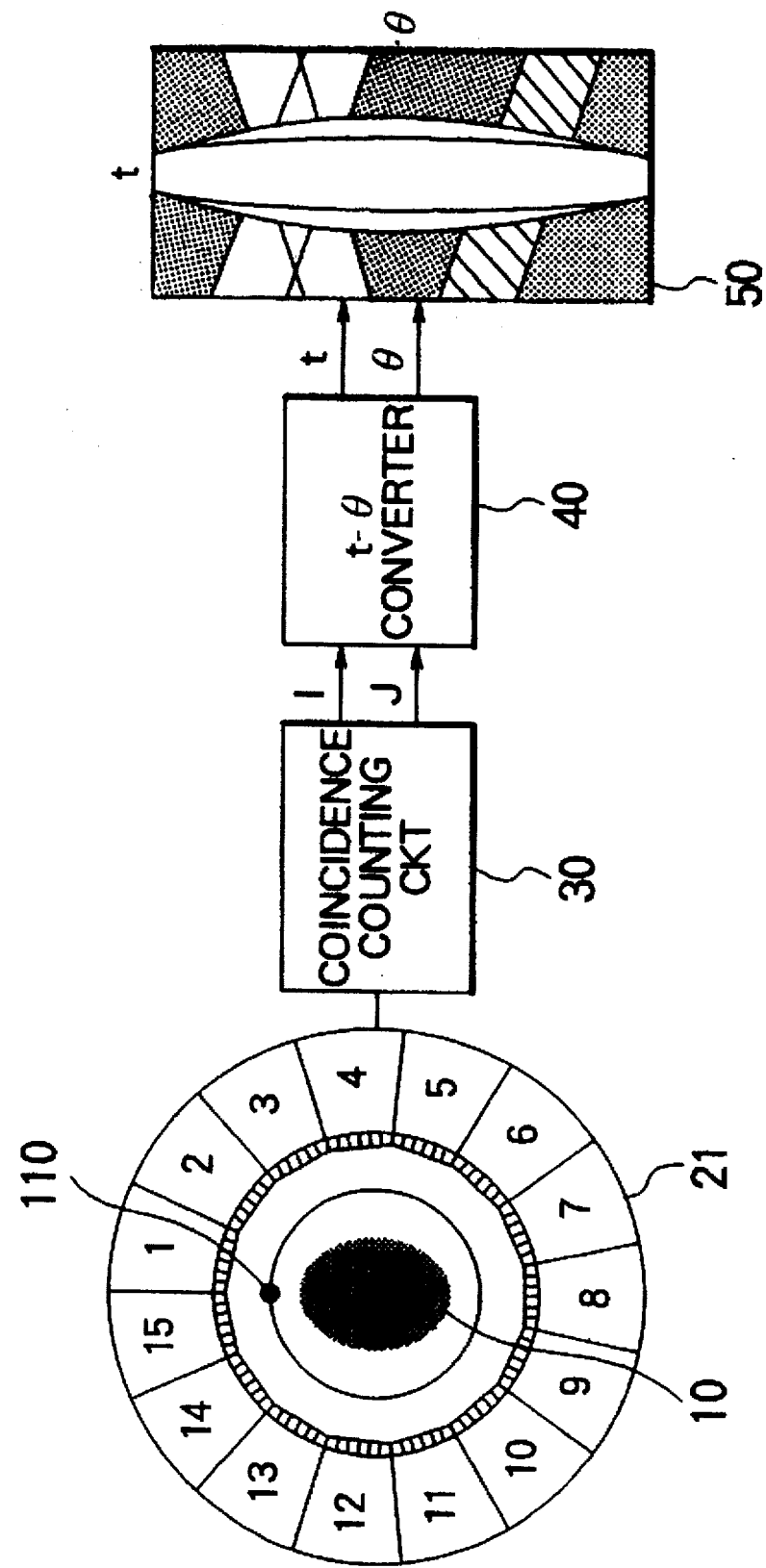
FIG. 9 a block diagram to explain transmission measurement in the 2D-PET of FIG. 6.

In the detector ring, normally, detection sensitivities of the respective photon detectors are not constant but inconsistent. Thus, sensitivity correction of photon detectors and absorption correction of the object will be explained referring to FIG. 7 to FIG. 9. FIG. 7 to FIG. 9 show only the detector ring, coincidence counting circuit, t–θ converting section, and t–θ memory as omitting the other constituent elements.

FIG. 7 is a block diagram to explain the emission measurement in the 2D-PET. As shown in FIG. 7, the object 100 charged with the RI radiation sources is measured as placed in the detector ring 21, and coincidence counting information is accumulated through the coincidence counting circuit 30 and t–θ converting section 40, which will be called the emission measurement. The data accumulated in the t–θ memory 50 thereby is called emission data, which will be represented by E(t, θ).

FIG. 8 is a block diagram to explain the blank measurement in the 2D-PET. As shown in FIG. 8, without placing the object in the detector ring 21, the RI radiation source 10 for calibration is rotated about the center axis of ring in the detector ring 21 to make imitational parallel light incident into each photon detector, thereby performing measurement (blank measurement). Data accumulated in the t–θ memory 50 in this manner (blank data B(t, θ)) indicates detection sensitivity variations of the photon detector pairs. Sensitivity correction is effected by dividing the emission data E(t, θ) by the blank data B(t, θ).

Further, photon absorption of object can be corrected as follows. FIG. 9 is a block diagram to explain the transmission measurement in the 2D-PET. As shown in FIG. 9, the object 100 without RI radiation source is placed at the same position as upon the emission measurement in the detector ring 21, and the RI radiation source 10 for calibration is rotated in the detector ring 21 in the same manner as in the blank measurement to perform measurement (transmission measurement), thereby acquiring data (transmission data T(t, θ)) as accumulated in the t–θ memory 50. An absorption coefficient on each coincidence counting line is obtained by dividing this transmission data T(t, θ) by the blank data B(t, θ), and absorption correction is effected by dividing the emission data E(t, θ) by the absorption coefficients.

In the transmission measurement, the statistical accuracy is heavily degraded because the weak RI radiation source is subject to further absorption by the object so as to decrease detection of photon pairs obtained. As a countermeasure, T(t, θ)/B(t, θ) is subjected to smoothing by a filter or the like.

The true projection data P(t, θ) after the sensitivity correction and absorption correction as described is expressed as follows, using the emission data E(t, θ), blank data B(t, θ), and transmission data T(t, θ).

$$P = (E/B)\langle T/B\rangle \qquad (1)$$

Here, symbol <> means the smoothing. The same is also applied in the case of 3D-PET.

As explained above, the 2D-PET of the present embodiment can perform the body motion correction for the object in motion and the sensitivity correction of emission data with accuracy, thereby enabling to obtain an accurate reconstructed image.

Here, the coincidence counting circuit 30, receiving signals from the respective photon detectors $D_k$ (k=1, 2, 3, ..., n), recognizes that two photon detectors in the detector ring 21 coincidently detected a photon pair having the predetermined energy (511 keV), appearing upon annihilation of an electron-positron pair, and outputs detector identification signals I and J respectively indicating these two photon detectors at that time, as detector pair identification signals (I, J).

The sensitivity data producing section 80, receiving the detector pair identification signals (I, J) output from the coincidence counting circuit 30, cumulates a constant value ("1," for example) at an address corresponding to the detector pair identification signals (I, J). Continuing this for a certain period of time, photon pair detection frequencies are obtained for all detector pair identification signals (I, J), i.e., for all photon detector pairs, and the photon pair detection frequencies thus produced are stored as sensitivity data B(I, J).

This function of the sensitivity data producing section 80 is activated upon the blank measurement. Namely, the detector ring 21 detects photon pairs occurring from the calibration radiation source 10 rotating about the center axis of the detector ring 21 in the measurement space 22, and the sensitivity data producing section 80 receives the detector pair identification signals (I, J) output from the coincidence counting circuit 30 to produce the sensitivity data B(I, J).

The cumulative data producing section 90, receiving the detector pair identification signals (I, J), takes the sensitivity data B(I, J) corresponding to the detector pair identification signals (I, J) out of the sensitivity data producing section 80 and outputs cumulative data C(I, J) inversely proportional to the values of sensitivity data B(I, J). Namely, there is the following relation for all (I, J) between the sensitivity data B(I, J) and the cumulative data C(I, J).

$$C(I, J) = a/B(I, J) \qquad (2)$$

Here, a is an arbitrary constant.

Such a function of the cumulative data producing section 90 is activated upon the emission measurement and upon the transmission measurement. Namely, the detector ring 21 detects photon pairs occurring from the object 100 with the RI radiation sources injected, as placed in the measurement space 22, and the cumulative data producing section 90 receives the detector pair identification signals (I, J) output from the coincidence counting circuit 30 to produce the cumulative data C(I, J) and output it to the t–θ memory 50.

The cumulative data C(I, J) may be preliminarily obtained by Eq. (2) and stored for all photon detector pairs (I, J) after end of the blank measurement and before start of the emission measurement or transmission measurement, or the cumulative data C(I, J) may be calculated by Eq. (2) to output the result every input of detector pair identification signals (I, J).

The detector pair identification signals (I, J) are also supplied to the t–θ converting section (coordinate converting section) 40, and are mapped to a position on the t–θ plane with the two variables (t, θ) each as coordinate axes used for expressing a straight line connecting two photon detectors having detected each photon pair indicated by the detector pair identification signals (I, J) by the polar coordinate system set in the measurement space 22 in the detector ring 21. This t–θ converting section 40 also receives the position-direction data output from the body motion measuring section 23 to compensate the coordinate data for the body motion of the object 100 and outputs values of the mapped position (T, Θ) on the t–θ plane as coordinate data to the t–θ memory 50.

The t–θ memory (projection data storing section) 50 for storing the projection data receives the coordinate values (t, θ) output from the t–θ converting section 40 in accordance with the detector pair identification signals (I, J) output from the coincidence counting circuit 30 as to a photon pair having been detected by the detector ring 21, and the cumulative data C(I, J) output from the cumulative data producing section 90 in accordance with the detector pair identification signals (I, J) similarly, and cumulates the cumulative data C(I, J) on the projection data stored at the address in the memory space corresponding to the coordinate values (t, θ). Such a function of the t–θ memory 50 is activated upon the emission measurement and upon the transmission measurement.

The projection data accumulated in the t–θ memory 50 of the PET according to the present invention in this manner is usually not integers but decimals. Accordingly, the t–θ memory 50 of the 2D-PET according to the present embodiment is preferably an integer type or floating-point type memory of 32-bit or 64-bit accuracy, for example. The projection data stored in the t–θ memory of the conventional PET was integer type data of 16-bit accuracy, whereas the present invention requires performance of higher speed and higher accuracy, which can be fully met by the present LSI technology.

Since the coordinate values (t, θ) are uniquely determined for the detector pair identification signals (I, J), B(I, J) and C(I, J) stated heretofore will be expressed hereinafter as B(t, θ) and C(t, θ), respectively.

Accordingly, against the emission data E(t, θ) and transmission data T(t, θ) obtained by cumulating the constant value "1" in the t–θ memory in the conventional 2D-PET to accumulate the projection data, the emission data E1(t, θ) and transmission data T1(t, θ), independently stored in the t–θ memory 50 in the 2D-PET according to the present embodiment, are given as follows.

$$E1(t, \theta) = E(t, \theta) \times C(t, \theta) \quad (3)$$
$$= a \times E(t, \theta)/B(t, \theta)$$

$$T1(t, \theta) = T(t, \theta) \times C(t, \theta) \quad (4)$$
$$= a \times T(t, \theta)/B(t, \theta)$$

Namely, the emission data E1(t, θ) stored in the t–θ memory 50 is data obtained after the sensitivity correction with the blank data B(t, θ). The true radiation sum P1(t, θ), obtained by further effecting the absorption correction concerning the object by the image reconstructing section 60, is immediately obtained from the following equation.

$$P1(t,\theta)=E1(t,\theta)/T1(t,\theta) \quad (5)$$

The image reconstructing section 60 for reconstructing an image of density distribution of RI radiation sources in the object 100 produces reconstructed image data indicating a spatial distribution of photon pair occurrence frequencies in the object 100 as observed from the predetermined direction θ of the polar coordinate system set in the measurement space 22 in the detector ring 21 from the emission data E1(t, θ) accumulated in the t–θ memory 50 or from the radiation sum data P1(t, θ) obtained after the absorption correction process. The image displaying section 70 displays a reconstructed image as taking in this reconstructed image data.

Figure 10:
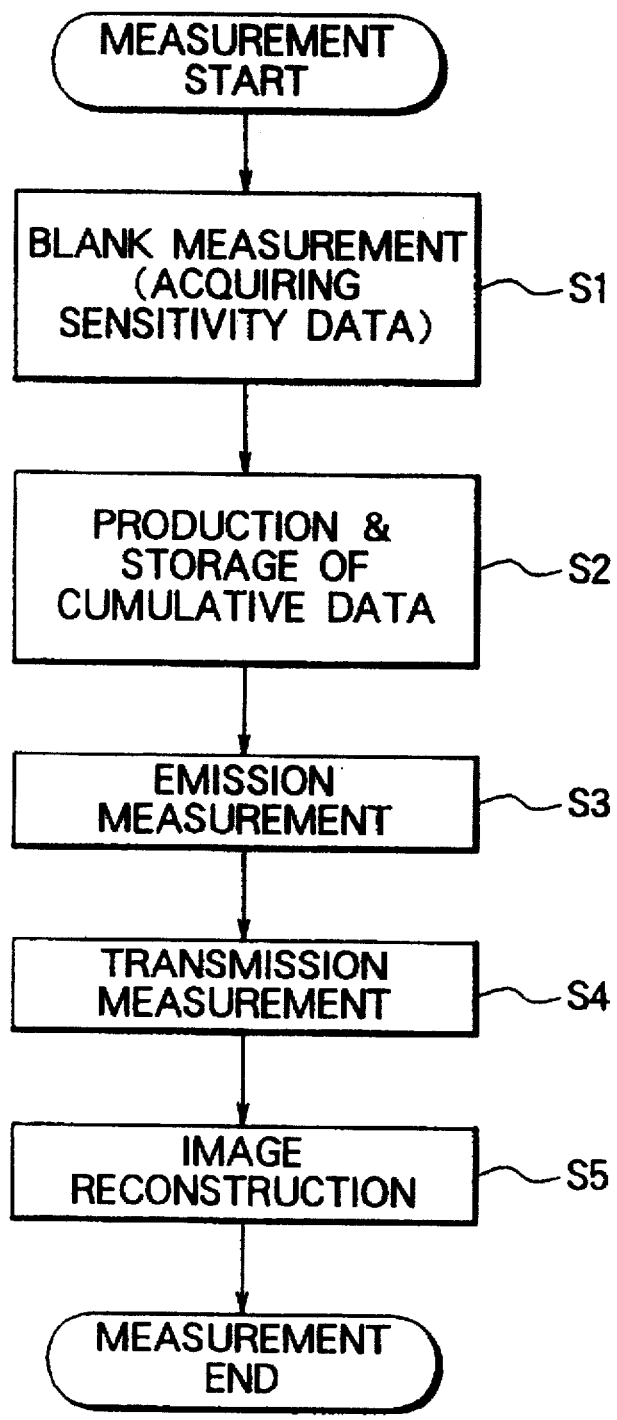
FIG. 10 is a flow chart to show measurement procedures in the 2D-PET of FIG. 1.

Next explained are the operation of the 2D-PET according to the present embodiment and the measurement method using this 2D-PET. FIG. 10 is the flowchart of measurement procedures in the 2D-PET.

As shown in FIG. 10, the blank measurement is first carried out at step S1 to acquire the sensitivity data B(I, J). Namely, without placing the object 100 in the measurement space 22, imitational parallel light is produced by rotating the calibration radiation source 10 about the center axis on the reference surface of the detector ring 21 by the rotating mechanism 24. In that state, photon pairs occurring from the calibration radiation source 10 are detected by many photon detectors constituting the detector ring 21 to be subjected to energy discrimination in the coincidence counting circuit 30.

The detector pair identification signals (I, J) indicating a photon detector pair having detected a photon pair, output from the coincidence counting circuit 30, are supplied to the sensitivity data producing section 80, and the constant value ("1," for example) is cumulated at the address corresponding to the detector pair identification signals (I, J). Continuing this for a certain period of time, photon pair detection frequencies are attained for all detector pair identification signals (I, J), i.e., for all photon detector pairs, thus obtaining the sensitivity data B(I, J).

After completion of the blank measurement, the cumulative data C(I, J) is calculated from the sensitivity data B(I, J) obtained by the blank measurement (step S1), based on Eq. (2), at step S2, and is stored in the cumulative data producing section 90.

Subsequently, at step S3 the emission measurement is carried out to acquire the emission data E1(I, J). Namely, with withdrawing or removing the calibration radiation source 10, the object 100 with the RI radiation sources injected is placed in the measurement space 22. In this state, photon pairs occurring from the object 100 are detected by the many photon detectors constituting the detector ring 21 to be subjected to energy discrimination in the coincidence counting circuit 30, and the coincidence counting circuit 30 outputs the detector pair identification signals (I, J) indicating a photon detector pair having detected a photon pair. Further, the body motion measuring section 23 measures the body motion of the object 100 to output the position-direction data.

The cumulative data producing section 90 receives the detector pair identification signals (I, J) to output corresponding cumulative data (I, J). At the same time, the detector pair identification signals (I, J) are also supplied to the t–θ converting section 40 together with the position-direction data indicating the position and direction of the object 100, output from the body motion measuring section 23, and the t–θ converting section 40 outputs coordinate values (t, θ) after compensated for the body motion of the object 100.

Then the coordinate values (t, θ) and cumulative data C(I, J) are supplied to the t–θ memory 50 to cumulate the cumulative data C(I, J) on the projection data stored at the corresponding address to the coordinate values (t, θ). The projection data accumulated after continuing this process for a certain period of time is the emission data E1(I, J).

In this manner, upon accumulating the projection data in the t–θ memory 50, the cumulative data C(I, J) for each photon detector pair is cumulated at a corresponding address to the coordinate values (t, θ) expressing, by the polar coordinate system, a straight line connecting a photon detector pair represented by the detector pair identification signals (I, J) at the point when the photons were detected. Accordingly, the body motion compensation of the object 100 and the sensitivity correction of the detector ring 21 are simultaneously effected at the stage of accumulation of the projection data in the t–θ memory 50.

Further, in the case of the absorption correction of the object 100 being also carried out, the transmission measurement is carried out at step S4 to acquire the transmission data Ti(I, J). Namely, the object 100 without RI radiation sources injected is placed in the measurement space 22, and imitational parallel light is produced by rotating the calibration radiation source 10 about the center axis of the detector ring 21 on the reference surface of the detector ring 21. In this state, the transmission data T1(t, θ) is acquired in the same manner as in the emission measurement.

Also in this case, similarly as in the case of the emission measurement, the body motion compensation of the object 100 and the sensitivity correction of the detector ring 21 are simultaneously carried out at the stage of accumulation of the projection data in the t–θ memory 50. It is noted that either the emission measurement (step S3) or the transmission measurement (step S4) can be performed first.

After completion of the above measurements, at step S5 the reconstructed image data is produced by the image reconstructing section 60, based on the emission data E1(t, θ) obtained by the emission measurement or based on the true radiation sum P1(t, θ) obtained according to Eq. (5) in the case of the absorption correction being also carried out, and a reconstructed image is indicated in the image displaying section 70.

In the case of the detector ring comprised of a monolayer ring as in the 2D-PET of the present embodiment, the motion of the object is equivalent to the motion of the detector ring. Especially, the motion of the object in the direction along the center axis of the detector ring is equivalent to the motion of the detector ring in the direction along the center axis. Therefore, only one cross section can be measured with a fixed object, whereas many sections can be measured with a moving object. Namely, the apparatus may be considered as a pseudo 3D-PET. However, since the detector ring is actually of a monolayer, the detection sensitivity of this 2D-PET is lower than the 3D-PET as described below.

Second Embodiment

Figure 11:
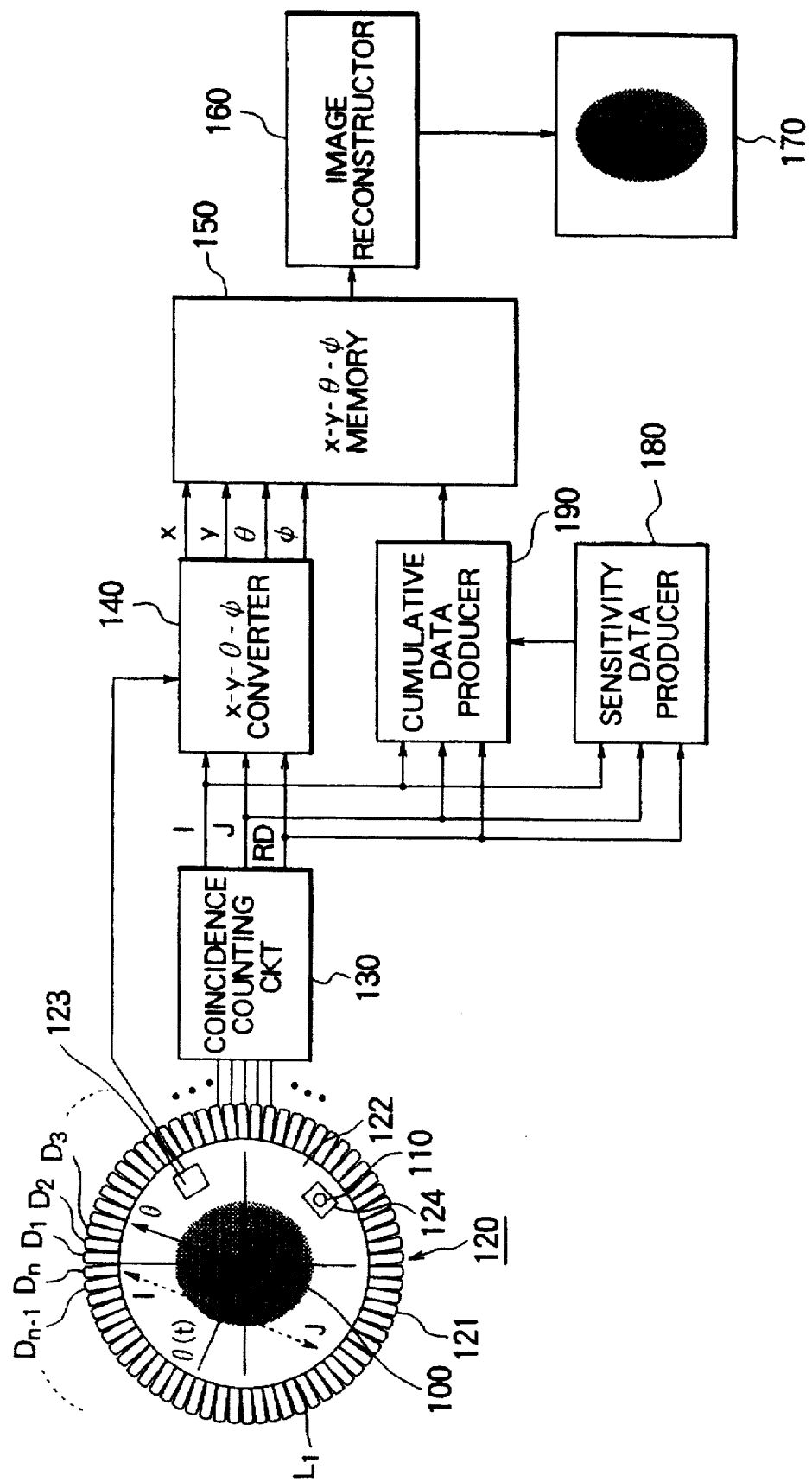
FIG. 11 is a block diagram to show the system structure of a three-dimensional positron emission computed tomography apparatus (3D-PET) of the second embodiment according to the present invention.
Figure 12:
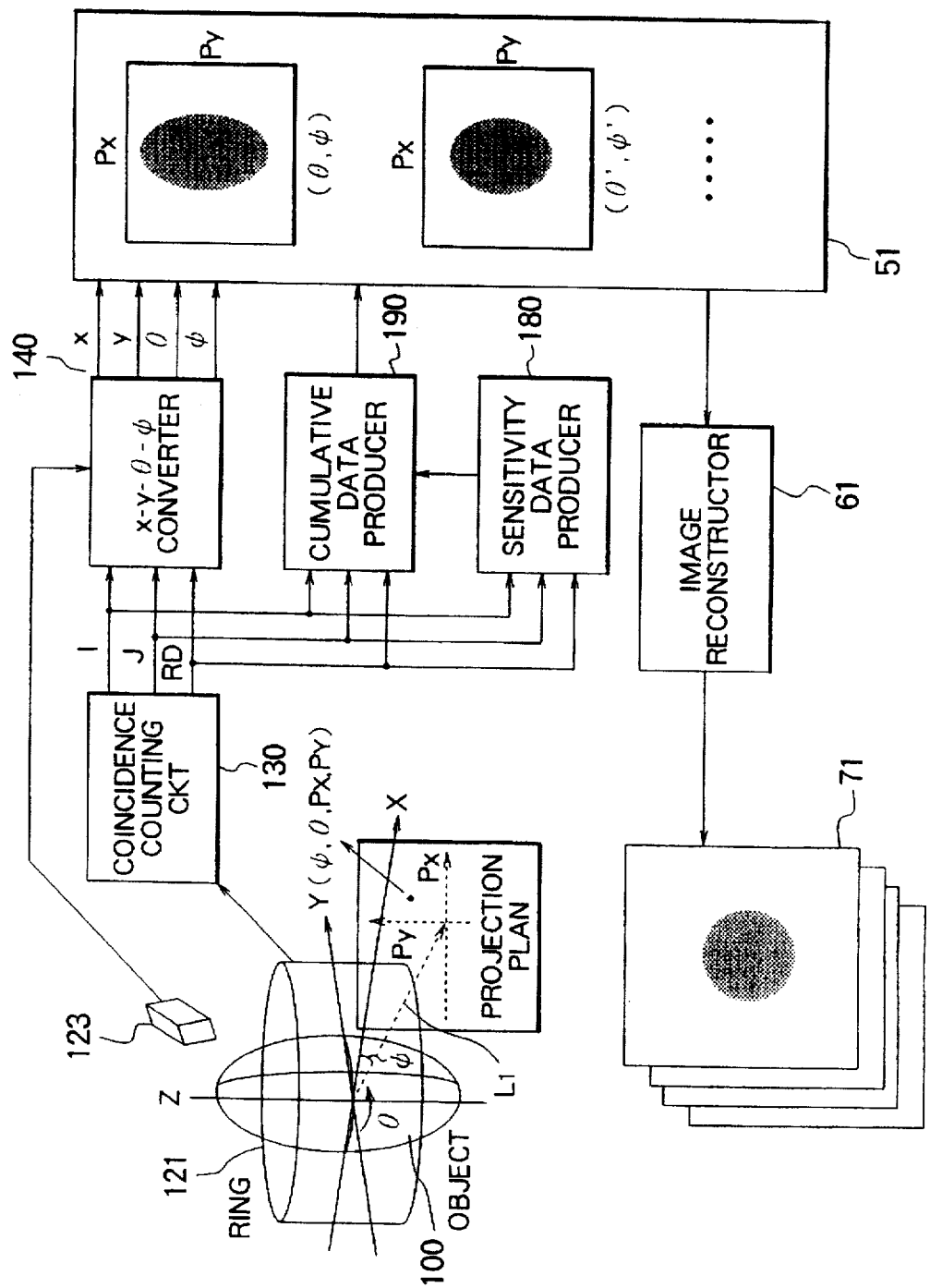
FIG. 12 is a block diagram to show the further detailed system structure of the 3D-PET of FIG. 11.

The three-dimensional positron emission computed tomography apparatus (3D-PET) of the present embodiment is used as moving the object relative to the stationary detector ring. FIG. 11 and FIG. 12 are block diagrams to show the system structure of the 3D-PET. In FIG. 12, the detector ring is schematically shown in cylindrical shape in order to clearly show the coordinate axes of the measurement space.

This 3D-PET detects photon pairs flying in all directions from each RI radiation source as well as those flying in directions along the reference plane of the detector ring from the RI radiation source contained in the object. Therefore, the 3D-PET of the present embodiment has a higher probability of capturing photon pairs emitted from the RI radiation sources as compared with the 2D-PET of the first embodiment, so that the 3D-PET of the present embodiment has higher detection sensitivity but lower statistical noise. Therefore, the 3D-PET of the present embodiment does not require a lot of RI radiation sources injected into the object in order to improve the detection sensitivity, and is effective especially in the cases where the object is a living body.

As shown in FIG. 11, this 3D-PET comprises (1) a detecting section 120 having a detector ring 121 comprised of a lot of photon detectors, arranged in ring shape, for detecting photons, a body motion measuring section 123 for measuring the position and direction of object 100 to output position-direction data, a rotating mechanism 124 for rotating a radiation source for calibration 110 about the center axis of the detector ring 121 in a measurement space 122, etc. and (2) a coincidence counting circuit 130 for determining whether a photon pair detected by the detector ring 121 is one occurring with annihilation of an electron-positron pair, identifying a photon detector pair having detected the photon pair occurring with annihilation of the electron-positron pair, and outputting detector pair identification signals.

The 3D-PET further comprises (3) a sensitivity data producing section 180 for producing sensitivity data concerning all of the detector pair identification signals received from the coincidence counting circuit 130, (4) a cumulative data producing section 190 for outputting cumulative data inversely proportional to values of the sensitivity data received from the sensitivity data producing section 180, corresponding to the detector pair identification signals received from the coincidence counting circuit 130, and (5) an x-y-θ-ψ converting section 140 for performing conversion of coordinates to obtain coordinate values (x, y, θ, ψ) as expressing a straight line (detector line) connecting each photon detector pair, identified by the coincidence counting circuit 130, with each other by polar coordinates.

The 3D-PET further comprises (6) an x-y-θ-ψ memory 150 for cumulating the cumulative data received from the cumulative data producing section 190 at an address corresponding to the coordinate values (x, y, θ, ψ) after converted into by the x-y-θ-ψ converting section 140 to accumulate it as projection data, (7) an image reconstructing section 160 for producing reconstructed image data based on the projection data accumulated in the x-y-θ-ψ memory 150, and (8) an image displaying section 170 for displaying a reconstructed image based on the reconstructed image data produced by the image reconstructing section 160.

The detector ring 121 is of a multilayer ring in which m monolayer rings $R_l$ (l=1, 2, ..., m), each comprised of n photon detectors $D_k$ (k=1, 2, ..., n) arranged in ring shape, are stacked. A light receiving surface of each photon detector is placed as faced to the object 100 set in the measurement space 122 located around the center axis thereof. The photon detectors $D_{lk}$ (l=1, 2, ..., m; k=1, 2, ..., n) which are the n photon detectors $D_k$ in the m monolayer rings $R_l$ each are connected to the coincidence counting circuit 130 by a signal line.

Figure 13:
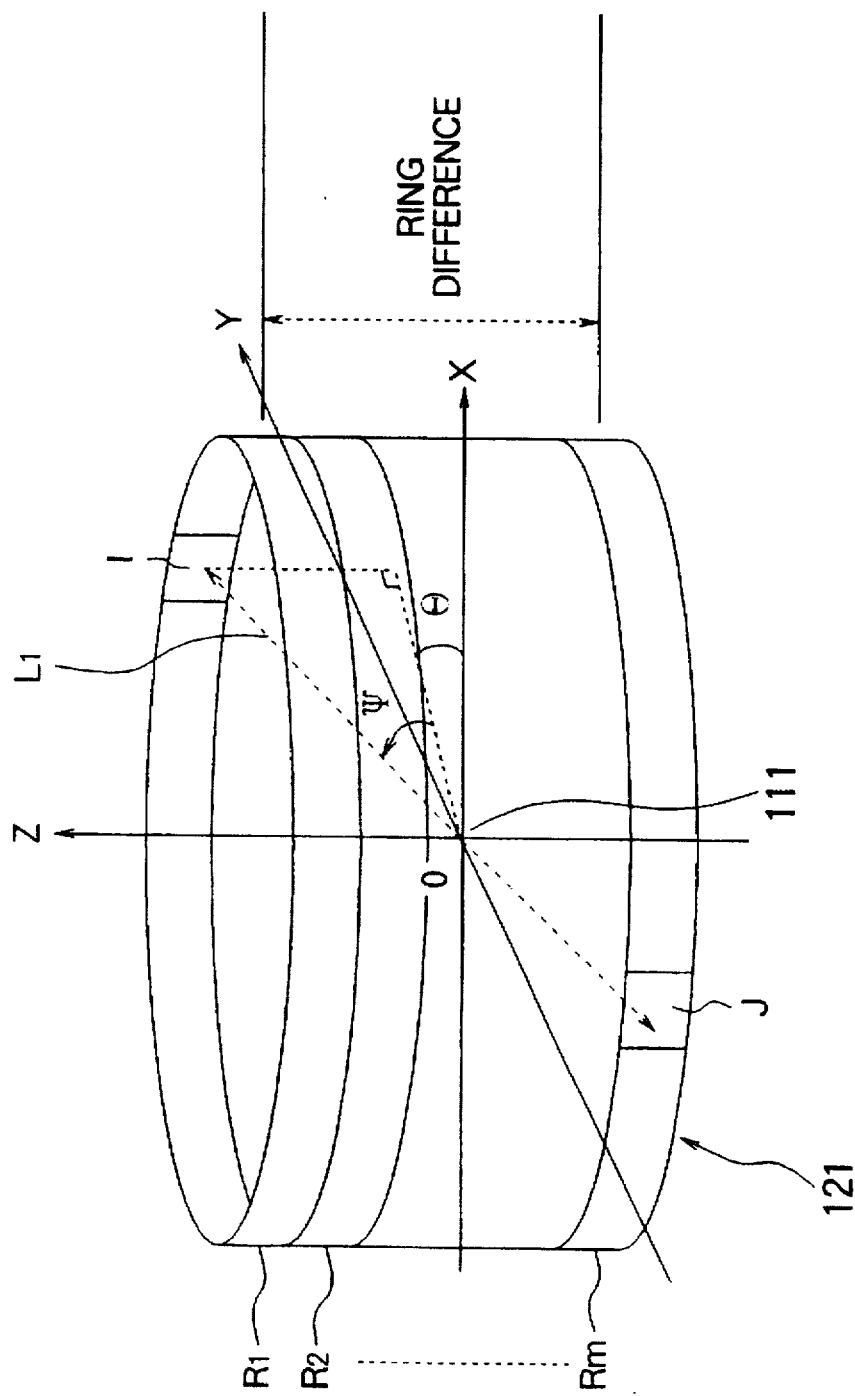
FIG. 13 is a perspective view to show the structure of the detector ring in the 3D-PET of FIG. 11.

FIG. 13 is a perspective view to show the structure of the detector ring in the 3D-PET. As shown in FIG. 13, the multilayer ring 121 of the 3D-PET is a ring in which multiple monolayer rings $R_1, R_2, ..., R_m$ of photon detectors, constructed in the same manner as in the above first embodiment and arranged with the XY plane thereof being on the reference surface, are stacked along the Z-axis direction. A photon pair emitted from an RI radiation source 111 contained in the object 100 and flying in directions along the straight line L1 can also be coincidently counted by two photon detectors belonging to respective monolayer rings $R_p$, $R_q$ (p $^{16}$q) different from each other.

When certain two photon detectors in the multilayer ring 121 coincidently detect a photon pair with the energy 511 keV emitted from the RI radiation source 111, the coincidence counting circuit 130 outputs detector identification signals (I, J) respectively indicating the two photon detectors and a difference signal RD (Ring Difference) between two monolayer rings to which the two photon detectors belong.

These detector identification signals (I, J) and ring difference signal RD are supplied to the x-y-θ-ψ converting section 140 to be converted into a mapping position (X, Y, Θ, Ψ) on the x-y-θ-ψ space with the coordinate axes being the four variables (x, y, θ, ψ) used for expressing the straight line L1 connecting the two photon detectors having detected the photon pair by polar coordinates in the measurement space in the multilayer ring 121. Here, Θ and Ψ represent the direction of the straight line L1 while X and Y the position thereof by the orthogonal coordinate system on the projection plane normal to the straight line L1.

The x-y-θ-ψ memory 150 cumulates the predetermined value in the projection data stored at an address corresponding to this coordinate position (X, Y, Θ, Ψ). In this manner, the coincidence counting information about a pair of photons occurring at the RI radiation source 111 is accumulated as projection data in the x-y-θ-ψ memory 150. An image is reconstructed from this data by the image reconstructing section 160 and the thus reconstructed image is displayed in the image displaying section 170.

Figure 14:
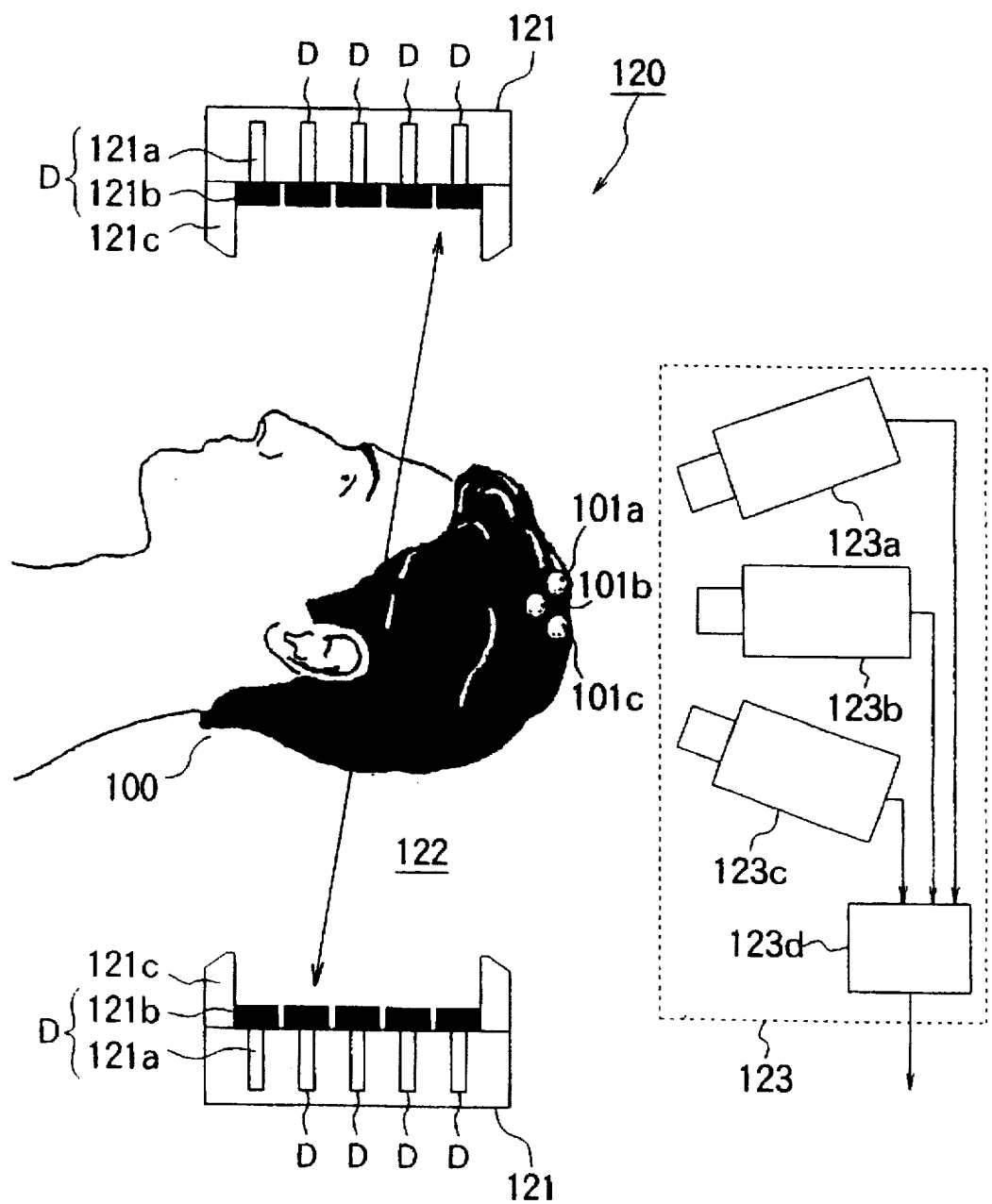
FIG. 14 is a sectional view to show the structure of the detecting section in the 3D-PET of FIG. 11.

FIG. 14 is a sectional view to show the structure of the detecting section in the 3D-PET. As shown in FIG. 14, the detecting section 120 comprises a detector ring 121 constructed as a multilayer ring comprised of many photon detectors D, and a body motion measuring section (position-direction measuring section) 123 for measuring the position and direction of the object 100.

The detector ring 121 detects photon pairs incident thereto from the measurement space 122 defined inside and outputs photon detection signals to the coincidence counting circuit 130. This detector ring 121 is constructed in such structure that multiple monolayer rings are stacked (in five layers in this FIG. 14), and each monolayer ring comprises a plurality of photon detectors D arranged in ring shape. Each photon detector D is comprised of a PMT (Photo-Multiplier Tube) 121a and a scintillator 121b set in a light-receiving surface of the PMT 121a. The light-receiving surface of each photon detector D is faced to the measurement space 122 in which the object 100 is placed.

Screening shields 121c are provided on the side surfaces of respective scintillators 121b of the uppermost and lowermost photon detectors with respect to the stack direction of photon detectors D. The screening shields 121c are provided for preventing a photon pair from leaking to the outside of the measurement space 122, but are arranged not to separate the monolayer rings from each other. This arrangement thus enables to detect a photon pair between different monolayer rings.

The body motion measuring section 123 measures the position and direction of the object 100 set in the measurement space 122 and outputs the position-direction data to the x-y-θ-ψ converting section 140. This body motion measuring section 123 is comprised of, for example, three optical distance-measuring sensors 123a to 123c each consisting of a light emitting element and a light receiving element, and a body motion data processing section 123d for outputting the position-direction data based on outputs therefrom.

The distance-measuring sensors 123a to 123c each are positioned in fixed relative positional relation to the detector ring 121, and they project respective light beams toward three markers 101a to 101c set at selected positions of the object 100 (on the head of a human body being the object 100 in FIG. 14) to receive reflected light therefrom and measure distances to these markers 101a to 101c. The distance data obtained from each of the three distance-measuring sensors 123a to 123c is supplied to the body motion data processing section 123d to obtain the position and direction of the object 100.

Image pickup cameras may be used as the body motion measuring section 123, and the position and direction of the object 100 may be obtained by analyzing images obtained thereby. As another example, acceleration sensors set at selected positions of the object 100 may be used as the body motion measuring section 123, and in this case, the position and direction of the object 100 can be obtained based on outputs from the acceleration sensors.

As shown in FIG. 11, the detecting section 120 further comprises a calibration radiation source 110 used for blank measurement and transmission measurement, and a rotating mechanism 124 for rotating it about the center axis of the detector ring 121. This rotating mechanism 124 is constructed in the same manner as the rotating mechanism 24 in the above first embodiment, and consists of, for example, a supporting mechanism for supporting the calibration radiation source 110 as being capable of rotating it about the center axis of the detector ring 121, a belt for transmitting the rotational force to the supporting mechanism, and a motor for generating the rotational force.

The calibration radiation source 110, when used (upon blank measurement and upon transmission measurement), is rotated about the center axis of the detector ring 121 on the reference surface of the detector ring 121, whereby the photon detector pairs can detect photon pairs occurring from the calibration radiation source 110. On the other hand, when not used (upon emission measurement), the calibration radiation source 110 is kept at a withdrawn position where the photon pairs occurring from the calibration radiation source 110 do not reach any photon detectors. Alternatively, the calibration radiation source 110 may be removed from this apparatus.

Here, the coincidence counting circuit 130, receiving signals from the respective photon detectors $D_{ik}$ (l=1, 2, . . ., m; k=1, 2, 3, . . . , n), recognizes that two photon detectors in the detector ring 121 coincidently detected a photon pair having the predetermined energy (511 keV), appearing upon annihilation of an electron-positron pair, and outputs detector identification signals I and J (i.e., detector pair identification signals (I, J)) respectively indicating these two photon detectors at that time, and the ring difference signal RD.

The sensitivity data producing section 180, receiving the detector pair identification signals (I, J) and the ring difference signal RD output from the coincidence counting circuit 130, cumulates a constant value ("1," for example) at an address corresponding to the detector pair identification signals (I, J). Continuing this for a certain period of time, photon pair detection frequencies are obtained for all detector pair identification signals (I, J), i.e., for all photon detector pairs, and the photon pair detection frequencies thus produced are stored as sensitivity data B(I, J).

This function of the sensitivity data producing section 180 is activated upon the blank measurement. Namely, the detector ring 121 detects photon pairs occurring from the calibration radiation source 110 rotating about the center axis of the detector ring 121 in the measurement space 122, and the sensitivity data producing section receives the detector pair identification signals (I, J) output from the coincidence counting circuit 130 to produce the sensitivity data B(I, J).

The cumulative data producing section 190, receiving the detector pair identification signals (I, J) and ring difference signal RD, takes the sensitivity data B(I, J) corresponding to the detector pair identification signals (I, J) out of the sensitivity data producing section 180 and outputs cumulative data C(I, J) inversely proportional to the values of sensitivity data B(I, J). Namely, there is the relation expressed by Eq. (2) for all (I, J) between the sensitivity data B(I, J) and the cumulative data c(I, J).

Such a function of the cumulative data producing section 190 is activated upon the emission measurement and upon the transmission measurement. Namely, the detector ring 121 detects photon pairs occurring from the object 100 with the RI radiation sources injected, as placed in the measurement space 122, and the cumulative data producing section 190 receives the detector pair identification signals (I, J) output from the coincidence counting circuit 130 to produce the cumulative data C(I, J) and output it to the x-y-θ-ψ memory 150.

The cumulative data C(I, J) may be preliminarily obtained by Eq. (2) and stored for all (I, J) after end of the blank measurement and before start of the emission measurement or transmission measurement, or the cumulative data C(I, J) may be calculated by Eq. (2) to output the result every input of detector pair identification signals (I, J).

The detector pair identification signals (I, J) and ring difference signal RD are also supplied to the x-y-θ-ψ converting section (coordinate converting section) 140, and are mapped to a position in the x-y-θ-ψ space with the four variables (x, y, θ, ψ) each as coordinate axes used for expressing a straight line connecting two photon detectors having detected each photon pair indicated by the detector pair identification signals (I, J) by the polar coordinate system set in the measurement space 122 in the detector ring 121. This x-y-θ-ψ converting section 140 also receives the position-direction data output from the body motion measuring section 123 to compensate the coordinate data for the body motion of the object 100 and outputs values of the mapped position (X, Y, Θ, Ψ) on the x-y-θ-ψ space as coordinate data.

The x-y-θ-ψ memory (projection data storing section) 150 for storing the projection data receives the coordinate values (x, y, θ, ψ) output from the x-y-θψ converting section 140 in accordance with the detector pair identification signals (I, J) output from the coincidence counting circuit 130 as to a photon pair having been detected by the detector ring 121, and the cumulative data C(I, J) output from the cumulative data producing section 190 in accordance with the detector pair identification signals (I, J) similarly, and cumulates the cumulative data C(I, J) on the projection data stored at the address corresponding to the coordinate values (x, y, θ, ψ). Such a function of the x-y-θ-ψ memory 150 is activated upon the emission measurement and upon the transmission measurement.

The projection data accumulated in the x-y-θ-ψ memory 150 of the PET according to the present invention in this manner is usually not integers but decimals. Accordingly, the x-y-θ-ψ memory 150 of the 3D-PET according to the present embodiment is preferably an integer type or floating-point type memory of 32-bit or 64-bit accuracy, for example. The projection data stored in the x-y-θ-ψ memory of the conventional PET was integer type data of 16-bit accuracy, whereas the present invention requires performance of higher speed and higher accuracy, which can be fully met by the present LSI technology.

Since the coordinate values (x, y, θ, ψ) are uniquely determined for the detector pair identification signals (I, J), B(I, J) and C(I, J) stated heretofore will be expressed hereinafter as B(x, y, θ, ψ) and C(x, y, θ, ψ), respectively.

Accordingly, against the emission data E(x, y, θ, ψ) and transmission data T(x, y, θ, ψ) obtained by cumulating the constant value "1" in the x-y-θ-ψmemory in the conventional 3D-PET to accumulate the projection data, the emission data E1(x, y, θ, ψ) and transmission data T1(x, y, θ, ψ), independently stored in the x-y-θψ memory 150 in the 3D-PET according to the present embodiment, are given as follows.

$$E1(x, y, \theta, \psi) = E(x, y, \theta, \psi) \times C(x, y, \theta, \psi) \quad (6)$$
$$= a \times E(x, y, \theta, \psi)/B(x, y, \theta, \psi)$$

$$T1(x, y, \theta, \psi) = T(x, y, \theta, \psi) \times C(x, y, \theta, \psi) \quad (7)$$
$$= a \times T(x, y, \theta, \psi)/B(x, y, \theta, \psi)$$

Namely, the emission data E1(x, y, θ, ψ) stored in the x-y-θ-ψ memory 150 is data obtained after the sensitivity correction with the blank data B(x, y, θ, ψ). The true radiation sum P1(x, y, θ, ψ), obtained by further effecting the absorption correction concerning the object by the image reconstructing section 160, is immediately obtained from the following equation.

$$P1(x,y,\theta,\psi)=E1(x,y,\theta,\psi)/T1(x,y,\theta,\psi) \quad (8)$$

The image reconstructing section 160 for reconstructing an image of density distribution of RI radiation sources in the object 100 produces reconstructed image data indicating a spatial distribution of photon pair occurrence frequencies in the object 100 as observed from the predetermined directions θ, ψ of the polar coordinate system set in the measurement space 122 in the detector ring 121 from the emission data E1(x, y, θ, ψ) accumulated in the x-y-θψ memory 150 or from the radiation sum data P1(x, y, θ, ψ) obtained after the absorption correction process, and the image displaying section 170 displays a reconstructed image as taking in this reconstructed image data.

Next explained are the operation of the 3D-PET according to the present embodiment and the measurement method using this 3D-PET. The measurement procedures in the 3D-PET according to the present embodiment are substantially the same as in the flowchart of the above first embodiment shown in FIG. 10.

The blank measurement is first carried out at step S1 to acquire the sensitivity data B(I, J). Namely, without placing the object 100 in the measurement space 122, imitational parallel light is produced by rotating the calibration radiation source 110 about the center axis on the reference surface of the detector ring 121 by the rotating mechanism 124. In that state, photon pairs occurring from the calibration radiation source 110 are detected by many photon detectors constituting the detector ring 121 to be subjected to energy discrimination in the coincidence counting circuit 130.

The detector pair identification signals (I, J) indicating a photon detector pair having detected a photon pair and ring difference signal RD, output from the coincidence counting circuit 130, are supplied to the sensitivity data producing section 180, and the constant value ("1," for example) is cumulated at the address corresponding to the detector pair identification signals (I, J). Continuing this for a certain period of time, photon pair detection frequencies are attained for all detector pair identification signals (I, J), i.e., for all photon detector pairs, thus obtaining the sensitivity data B(I, J).

After completion of the blank measurement, the cumulative data C(I, J) is calculated from the sensitivity data B(I, J) obtained by the blank measurement (step S1), based on Eq. (2), at step S2, and is stored in the cumulative data producing section 190.

Subsequently, at step S3 the emission measurement is carried out to acquire the emission data E1(I, J). Namely, with withdrawing or removing the calibration radiation source 110, the object 100 with the RI radiation sources injected is placed in the measurement space 122. In this state, photon pairs occurring from the object 100 are detected by the many photon detectors constituting the detector ring 121 to be subjected to energy discrimination in the coincidence counting circuit 130, and the coincidence counting circuit 130 outputs the detector pair identification signals (I, J) indicating a photon detector pair having detected a photon pair, and the ring difference signal RD. Further, the body motion measuring section 123 measures the body motion of the object 100 to output the position-direction data.

The cumulative data producing section 190 receives the detector pair identification signals (I, J) and ring difference signal RD to output corresponding cumulative data (I, J). At the same time, the detector pair identification signals (I, J) and ring difference signal RD are also supplied to the x-y-θ-ψ converting section 140 together with the position-direction data indicating the position and direction of the object 100, output from the body motion measuring section 123, and the x-y-θ-ψ converting section 140 outputs coordinate values (x, y, θ, ψ) after compensated for the body motion of the object 100.

Then the coordinate values (x, y, θ, ψ) and cumulative data C(I, J) are supplied to the x-y-θ-ψ memory 150 to cumulate the cumulative data C(I, J) on the projection data stored at the corresponding address to the coordinate values (x, y, θ, ψ). The projection data accumulated after continuing this process for a certain period of time is the emission data E1(I, J).

In this manner, upon accumulating the projection data in the x-y-θ-ψ memory 150, the cumulative data C(I, J) for each photon detector pair is cumulated at a corresponding address to the coordinate values (x, y, Θ, ψ) expressing, by the polar coordinate system, a straight line connecting a photon detector pair represented by the detector pair identification signals (I, J) at the point when the photons were detected. Accordingly, the body motion compensation of the object 100 and the sensitivity correction are simultaneously effected at the stage of accumulation of the projection data in the x-y-θ-ψ memory 150.

Further, in the case of the absorption correction of the object 100 being also carried out, the transmission measurement is carried out at step S4 to acquire the transmission data T1(I, J). Namely, the object 100 without RI radiation sources injected is placed in the measurement space 122, and imitational parallel light is produced by rotating the calibration radiation source 110 about the center axis of the detector ring 121 on the reference surface of the detector ring 121. In this state, the transmission data T1(x, y, θ, ψ) is acquired in the same manner as in the emission measurement.

Also in this case, similarly as in the case of the emission measurement, the body motion compensation of the object 100 and the sensitivity correction are simultaneously carried out at the stage of accumulation of the projection data in the x-y-θ-ψ memory 150. It is noted that either the emission measurement (step S3) or the transmission measurement (step S4) can be performed first.

After completion of the above measurements, at step S5 the reconstructed image data is produced by the image reconstructing section 160, based on the emission data E1(x, y, θ, ψ) obtained by the emission measurement or based on the true radiation sum P1(x, y, θ, ψ) obtained according to Eq. (8) in the case of the absorption correction being also carried out, and a reconstructed image is indicated in the image displaying section 170.

The present invention is not limited to the above-stated 2D-PET, 3D-PET, and the like in the various embodiments, but can be applied to the PETs of other types.

For example, the present invention can be applied to a 2D-PET with the detector ring comprised of multilayer rings. The 2D-PET with the detector ring of multilayer rings can be considered to be substantially equivalent to such structure that a plurality of 2D-PETs each consisting of a monolayer ring are stacked. Also in this case, the motion of the object is equivalent to the motion of the detector ring. Especially, the motion of the object in the direction along the center axis of ring is equivalent to the motion of the detector ring in the direction along the center axis. Accordingly, only specific cross sections can be measured with a fixed object, whereas with a moving object, many cross sections can be measured within the range of the body motion, which can improve the spatial measurement resolution. Namely, this can be said as a pseudo 3D-PET.

Figure 15:
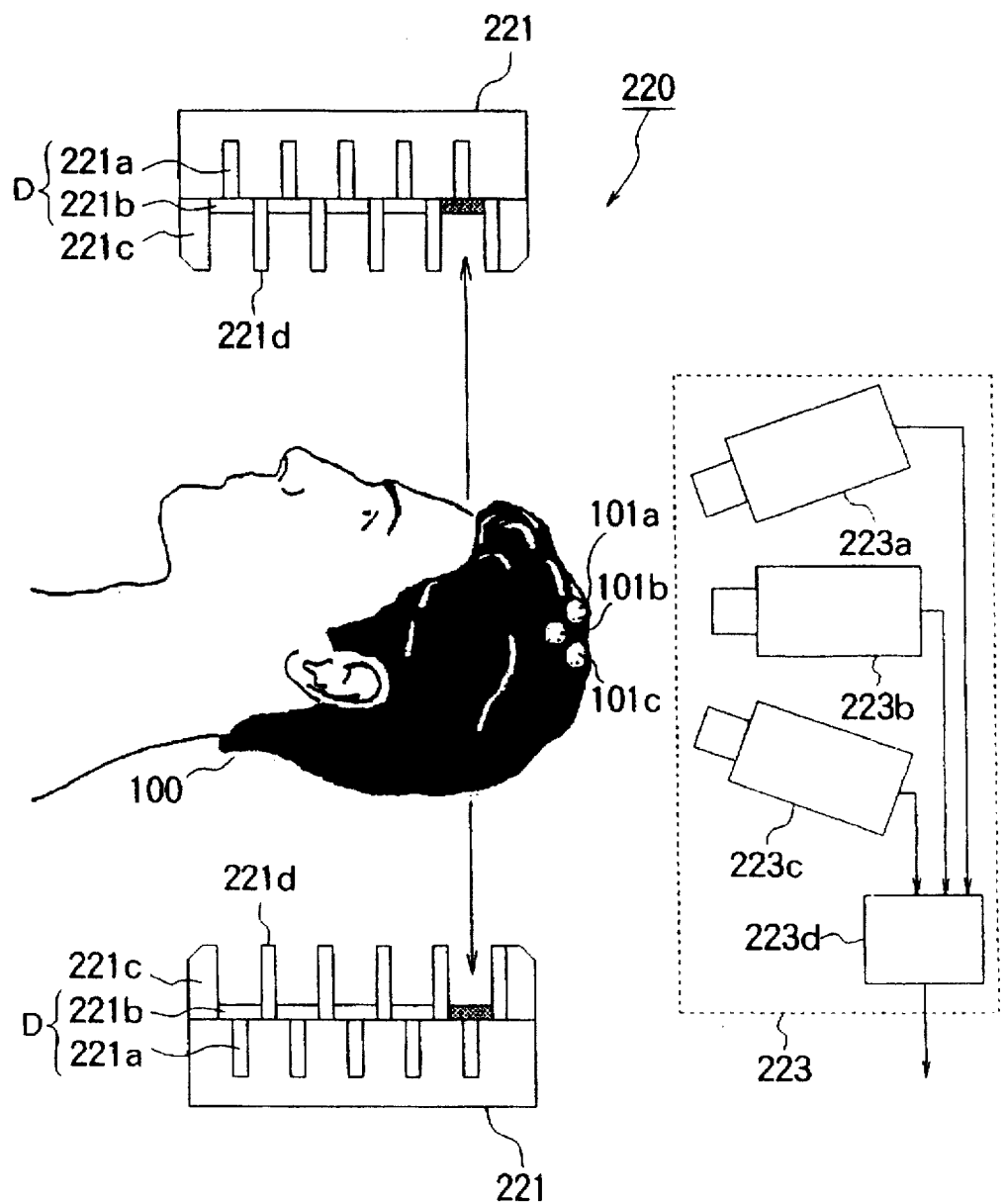
FIG. 15 is a sectional view to show the structure of the detecting section in a modification of the 2D-PET of FIG. 1.

FIG. 15 is a sectional view to show the structure of the detecting section in a modification of the 2D-PET of the above first embodiment. As shown in FIG. 15, a detector ring 221 in the detecting section 220 is constructed in such structure that a plurality of monolayer rings are stacked with a screening shield inbetween. In each monolayer ring, a plurality of photon detectors D are arranged in ring shape. Each photon detector D is comprised of a PMT 221a and a scintillator 221b set on a light receiving surface of this PMT 221a, and the light receiving surface is directed to the measurement space in which the object 100 is placed.

Screening shields 221c are arranged on the side surfaces of scintillators 221b of the uppermost and lowermost photon detectors along the stack direction of the photon detectors D. The screening shields 221c are provided for preventing a photon pair from leaking to the outside of the measurement space. Further, screening shields 221d are arranged between photon detectors along the stack direction of photon detectors D. The screening shields 221d are provided for optically separating the monolayer rings of the detector ring 221 from each other.

Therefore, the 2D-PET having the multilayer ring as the detector ring can also perform the same operation as in the above second embodiment, first carrying out the blank measurement to acquire the sensitivity data B(I, J) and further to produce the cumulative data C(I, J), thereafter carrying out the emission measurement (and transmission measurement) to cumulate the predetermined value in the cumulative data C(I, J) corresponding to a photon detector pair having detected a photon pair, at an address of the x-y-θ-ψ memory obtained after compensation for the body motion of object, every detection of photon pair, and then carrying out the image reconstruction based on the projection data accumulated in the x-y-θ-ψ memory.

The foregoing explained the cases where the object was able to move freely, but the same can also be applied to, for example, the cases where the object is limited as to the freedom degrees of body motion or the cases where the object is permitted only to rotate about the center axis of detector ring. Explaining it with the case of the 2D-PET, the sensitivity data producing section and cumulative data producing section are the same as in the case of the above first embodiment. The body motion measuring section measures a rotational displacement Δθ of the object and the coincidence counting circuit outputs detector pair identification signals (I, J) indicating a photon detector pair having detected a photon pair.

The t-θ converting section (coordinate converting section) outputs coordinate values (t, θ) corresponding to the detector pair identification signals (I, J) as compensating for the rotational displacement Δθ of the object. The t-θ memory (projection data accumulating means) accumulates the projection data while cumulating the cumulative data output from the cumulative data producing section, at the address corresponding to the coordinate values (t, θ) output from the t–θ converting section. The projection data thus stored is data already subject to the both body motion correction and sensitivity correction, and therefore, an accurate reconstructed image can be obtained by reconstructing the image based on the data.

The invention can also be applied similarly to the cases where the ring moves in rotational motion or in wobbling motion. In this case, the body motion measuring section fixed to the detector ring measures the position and direction of the object or measures both the rotational position of the detector ring and the position and direction of the object, and, based on the relative motion between the detector ring and the object obtained thereby, the true radiation sum after the body motion compensation and sensitivity correction can be obtained in the same manner as in the above embodiments.

As detailed above, the positron emission computed tomography apparatus (PET) according to the present invention first carries out the blank measurement to detect photon pairs occurring from the calibration radiation source rotated by the calibration source rotating mechanism and to acquire the sensitivity data by the sensitivity data producing means, based on the photon detection frequencies obtained for all photon detector pairs as to the many photon detectors constituting the detector ring.

Subsequently, the apparatus carries out the emission measurement to detect photon pairs occurring from the object by the detector ring, the coincidence counting circuit outputs the detector pair identification signals indicating a photon detector pair having detected a photon pair, the coordinate values corresponding to the detector pair identification signals are output from the coordinate converting means as compensated for the body motion of the object, and at the same time, the cumulative data inversely proportional to the sensitivity data corresponding to the detector pair identification signals is output from the cumulative data producing means. Then the projection data accumulating means cumulates the cumulative data output from the cumulative data producing means at the address corresponding to the coordinate values output from the coordinate converting means. Then an image is reconstructed based on the projection data accumulated in the projection data accumulating means.

The above structure permits an accurate reconstructed image to be obtained by immediately performing the image reconstructing process based on the projection data accumulated in the projection data accumulating means even in the cases where the object is not fixed but moves during measurement, because the both body motion correction and sensitivity correction have been effected at the stage of cumulating the cumulative data in the projection data accumulating means. Accordingly, an accurate reconstructed image can be obtained without occurrence of artifact.

From the invention thus described, it will be obvious that the invention may be varied in many ways. Such variations are not to be regarded as a departure from the spirit and scope of the invention, and all such modifications as would be obvious to one skilled in the art are intended for inclusion within the scope of the following claims.

The basic Japanese Application No. 297816/1995 filed on Oct. 20, 1995 is hereby incorporated by reference.

What is claimed is:

1. A positron emission computed tomography apparatus comprising:

a detector ring comprised of a plurality of photon detectors arranged in ring shape around a predetermined center axis to surround a measurement space, each said photon detector detecting a photon incident thereto from said measurement space to output a photon detection signal corresponding to energy of said photon;

a rotating mechanism for relatively rotating a calibration radiation source for emitting a positron to generate a photon pair with annihilation of electron-positron pair, relative to said detector ring about the center axis of said detector ring in said measurement space;

a position-direction measuring section for measuring position and direction of an object set in said measurement space, relative to said detector ring, and outputting position-direction data corresponding to the position and direction of said object;

a coincidence counting circuit for performing energy discrimination to determine if photons detected by said detector ring are a photon pair generated with annihilation of electron-positron pair in said measurement space, based on said photon detection signals received from said detector ring, and outputting a detector pair identification signal corresponding to a photon detector pair of said detector ring each having detected the two photons constituting said photon pair;

a sensitivity data producing section for counting events of detection of photon pair for every photon detector pair of said detector ring each having detected the two photons constituting said photon pair, based on said detector pair identification signal received from said coincidence counting circuit, while without setting said object in said measurement space said rotating mechanism rotates said calibration radiation source relative to said detector ring, and producing and storing sensitivity data corresponding to photon pair detection frequencies for all photon detector pairs of said detector ring;

a cumulative data producing section for producing cumulative data having values inversely proportional to values of said sensitivity data taken out from said sensitivity data producing section and, with setting said object in said measurement space, outputting said cumulative data corresponding to the photon detector pair of said detector ring each having detected the two photons constituting said photon pair, based on said detector pair identification signal received from said coincidence counting circuit;

coordinate converting means for converting, based on said detector pair identification signal received from said coincidence counting circuit, distance and direction of a detector line being a straight line connecting the photon detector pair of said detector ring each having detected the two photons constituting said photon pair into coordinate values expressed by predetermined polar coordinates set in said measurement space, compensating the coordinate values of said detector line in correspondence to the position and direction of said object, based on said position-direction data received from said position-direction measuring section, and outputting coordinate data corresponding to the coordinate values of said detector line;

a projection data accumulating section for cumulating said cumulative data received from said cumulative data producing section at an address of a memory space corresponding to the coordinate values of said detector line, based on said coordinate data received from said coordinate converting means, and accumulating said cumulative data distributed in said memory space, as projection data; and an image reconstructing section for calculating a spatial distribution of photon pair occurrence frequencies with annihilation of electron-positron pair in said object, based on said projection data taken out of said projection data accumulating section, and producing reconstructed image data corresponding to said spatial distribution of photon pair occurrence frequencies.

2. The positron emission computed tomography apparatus according to claim 1, further comprising an image displaying section for displaying a reconstructed image indicating the spatial distribution of photon pair occurrence frequencies with annihilation of electron-positron pair in said object, based on said reconstructed image data taken out of said image reconstructing section.

3. The positron emission computed tomography apparatus according to claim 1, wherein said cumulative data section produces and stores said cumulative data having the values inversely proportional to the values of said sensitivity data corresponding to all photon detector pairs of said detector ring before said detector ring detects said photon pair for said object set in said measurement space.

4. The positron emission computed tomography apparatus according to claim 1, wherein said cumulative data section produces and outputs said cumulative data having the values inversely proportional to the values of said sensitivity data corresponding to the photon detector pair of said detector ring each having detected the two photons constituting said photon pair every time said detector ring detects said photon pair for said object set in said measurement space.

5. The positron emission computed tomography apparatus according to claim 1, wherein without intentionally setting said calibration radiation source in said measurement space and with setting said object containing a positron emission nuclide therein, said cumulative data section outputs, as emission data, said cumulative data corresponding to the photon detector pair of said detector ring each having detected the two photons constituting said photon pair, based on said detector pair identification signal received from said coincidence counting circuit.

6. The positron emission computed tomography apparatus according to claim 5, wherein with setting said object intentionally containing no positron emission nuclide in said measurement space and with rotating said calibration radiation source relative to said detector ring by said rotating mechanism, said cumulative data section outputs, as transmission data, said cumulative data corresponding to the photon detector pair of the detector ring each having detected the two photons constituting said photon pair, based on said detector pair identification signal received from said coincidence counting circuit.

7. The positron emission computed tomography apparatus according to claim 6, wherein said projection data accumulating section cumulates said emission data and said transmission data received from said cumulative data producing section independently of each other at two types of addresses in said memory space corresponding to the coordinate values of said detector line, based on said coordinate data received from said coordinate converting means, and said image reconstructing section calculates a ratio of said emission data and said transmission data as said spatial distribution of photon pair occurrence frequencies, based on said projection data taken out of said projection data accumulating section.

8. An image reconstructing method of positron emission computed tomography for detecting photon pairs occurring with annihilation of electron-positron pair in a measurement space and measuring a spatial distribution of occurrence frequencies of said photon pairs by a detector ring comprised of a plurality of photon detectors arranged in ring shape around a predetermined center axis to surround the measurement space, each said photon detector detecting a photon incident thereto from said measurement space to output a photon detection signal corresponding to energy of said photon, and a coincidence counting circuit for performing energy discrimination to determine if photons detected by said detector ring are a photon pair occurring with annihilation of electron-positron pair in said measurement space, based on said photon detection signals output from said detection ring, and outputting a detector pair identification signal corresponding to a photon detector pair of said detector ring each having detected two photons constituting said photon pair, comprising:

a first step of, without setting an object in said measurement space, relatively rotating a calibration radiation source for emitting a positron to generate a photon pair with annihilation of electron-position pair, relative to said detector ring about the center axis of said detector ring in said measurement space, thereafter counting events of detection of photon pair for every photon detector pair of said detector ring each having detected the two photons constituting said photon pair, based on said detector pair identification signal output from said coincidence counting circuit, and producing and storing sensitivity data corresponding to photon pair detection frequencies for all photon detector pairs of said detector ring;

a second step of, with setting said object in said measurement space, measuring position and direction of said object set in said measurement space, relative to said detector ring, converting, based on said detector pair identification signal output from said coincidence counting circuit, distance and direction of a detector line being a straight line connecting the photon detector pair of said detector ring each having detected the two photons constituting said photon pair into coordinate values expressed by predetermined polar coordinates set in said measurement space, producing cumulative data having values inversely proportional to values of said sensitivity data produced in said first step, cumulating said cumulative data at an address of a memory space corresponding to the coordinate values of said detector line compensated in correspondence to the position and direction of said object, and accumulating said cumulative data distributed in said memory space, as projection data; and a third step of calculating a spatial distribution of photon pair occurrence frequencies with annihilation of electron-positron pair in said object, based on said projection data produced in said second step, and producing reconstructed image data corresponding to said spatial distribution of photon pair occurrence frequencies.

9. The image reconstructing method of positron emission computed tomography according to claim 8, wherein said third step further comprising displaying a reconstructed image indicating the spatial distribution of photon pair occurrence frequencies with annihilation of electron-positron pair in said object, based on said reconstructed image data.

10. The image reconstructing method of positron emission computed tomography according to claim 8, wherein said second step comprises producing and storing said cumulative data having the values inversely proportional to the values of said sensitivity data corresponding to the all photon detector pairs of said detector ring before said detector ring detects said photon pair for said object set in said measurement space.

11. The image reconstructing method of positron emission computed tomography according to claim 8, wherein said second step comprises producing and outputting said cumulative data having the values inversely proportional to the values of said sensitivity data corresponding to the photon detector pair of said detector ring each having detected the two photons constituting said photon pair every time said detector ring detects said photon pair for said object set in said measurement space.

12. The image reconstructing method of positron emission computed tomography according to claim 8, wherein said second step comprises outputting, as emission data, said cumulative data corresponding to the photon detector pair of said detector ring each having detected the two photons constituting said photon pair, based on said detector pair identification signal received from said coincidence counting circuit, without intentionally setting said calibration radiation source in said measurement space and with setting said object containing a positron emission nuclide therein.

13. The image reconstructing method of positron emission computed tomography according to claim 12, wherein said second step comprises outputting, as transmission data, said cumulative data corresponding to the photon detector pair of said detector ring each having detected the two photons constituting said photon pair, based on said detector pair identification signal received from said coincidence counting circuit, with setting said object intentionally containing no positron emission nuclide in said measurement space and with rotating said calibration radiation source relative to said detector ring.

14. The image reconstructing method of positron emission computed tomography according to claim 13, wherein said second step comprises cumulating said emission data and said transmission data independently of each other at two types of addresses in said memory space corresponding to the coordinate values of said detector line, based on said coordinate data, and calculating a ratio of said emission data and said transmission data as said spatial distribution of photon pair occurrence frequencies, based on said projection data.

* * * * *